US009226939B2

(12) United States Patent
Stephens et al.

(10) Patent No.: US 9,226,939 B2
(45) Date of Patent: Jan. 5, 2016

(54) HISTONE INHIBITION

(75) Inventors: Ross Wentworth Stephens, Stirling Australian Capital Territory (AU); Christopher Richard Parish, Campbell Australian Capital Territory (AU); Craig Geoffrey Freeman, New South Wales (AU); Timothy John Senden, Aranda Australian Capital Territory (AU)

(73) Assignee: THE AUSTRALIAN NATIONAL UNIVERSITY, Acton, Australian Capital Territory (AU)

( * ) Notice: Subject to any disclaimer, the term of this patent is extended or adjusted under 35 U.S.C. 154(b) by 40 days.

(21) Appl. No.: 13/990,031

(22) PCT Filed: Nov. 29, 2011

(86) PCT No.: PCT/AU2011/001550
§ 371 (c)(1),
(2), (4) Date: Aug. 19, 2013

(87) PCT Pub. No.: WO2012/071611
PCT Pub. Date: Jun. 7, 2012

(65) Prior Publication Data
US 2013/0338097 A1   Dec. 19, 2013

Related U.S. Application Data

(60) Provisional application No. 61/418,826, filed on Dec. 1, 2010.

(51) Int. Cl.
| | | |
|---|---|---|
| *A61K 31/737* | (2006.01) | |
| *A61K 31/7016* | (2006.01) | |
| *A61K 31/702* | (2006.01) | |
| *A61K 31/727* | (2006.01) | |
| *A61K 31/70* | (2006.01) | |
| *A61K 31/715* | (2006.01) | |
| *A61K 31/724* | (2006.01) | |

(52) U.S. Cl.
CPC .............. *A61K 31/737* (2013.01); *A61K 31/70* (2013.01); *A61K 31/702* (2013.01); *A61K 31/7016* (2013.01); *A61K 31/715* (2013.01); *A61K 31/724* (2013.01); *A61K 31/727* (2013.01)

(58) Field of Classification Search
None
See application file for complete search history.

(56) References Cited

U.S. PATENT DOCUMENTS

| 4,847,338 A | 7/1989 | Linhardt et al. |
| 2005/0282775 A1 | 12/2005 | Kennedy |
| 2009/0117099 A1* | 5/2009 | Esmon et al. ............ 424/130.1 |

FOREIGN PATENT DOCUMENTS

| WO | 95/19176 A1 | 7/1995 |
| WO | 96/33726 A1 | 10/1996 |
| WO | WO 96/33726 | * 10/1996 |
| WO | 03/106503 A1 | 12/2003 |
| WO | 2006/015171 A2 | 2/2006 |
| WO | 2007/013123 A1 | 2/2007 |
| WO | 2007/062403 A2 | 5/2007 |
| WO | 2007/095688 A1 | 8/2007 |
| WO | WO 2007/095688 | * 8/2007 |
| WO | 2009/061918 A1 | 5/2009 |

OTHER PUBLICATIONS

Molinari, J. et al "Inhibition of antigen-induced airway hyper-responsiveness . . . " Am. J. Respir. Crit. Care Med. (1998) vol. 157, pp. 887-893.*
Freeman et al., "The accumulation of circulating histones on heparin sulphate in the capillary glycocalyx of the lungs," Biomaterials, 2013, 34(22), pp. 5670-5676.
Xu et al, "Extracellular histones are major mediators of death in sepsis," Nature Medicine, 2009, 15(11), 1318-1322.
International Search Report, PCT application No. PCT/AU2011/001550, mailed Jan. 19, 2012, 3 pages.
Cornet et al., "The role of heparin and allied compounds in the treatment of sepsis," Thromb Haemost, 2007, vol. 98, pp. 579-586.
Gennari et al., "Heparan Sulfate Increases Survival During Gut-Derived Sepsis by Decreasing Bacterial Translocation and Enhancing Host Defense," Shock, 1994, vol. 2(4), pp. 246-250.
Okazaki et al., "Pathophysiology of Sepsis and Recent Patents on the Diagnosis, Treatment and Prophylaxis for Sepsis," Recent Patents on Inflammation & Allergy Drug Discovery, 2009, vol. 3, pp. 26-32.
Wall et al., "Characterisation of the Anticoagulant Properties of a Range of Structurally Diverse Sulfated Oligosaccharides," Thrombosis Research, 2001, vol. 103, pp. 325-335.

* cited by examiner

*Primary Examiner* — Leigh Maier
(74) *Attorney, Agent, or Firm* — Kilpatrick Townsend & Stockton LLP

(57) ABSTRACT

The invention relates to a method of inhibiting the cytotoxic activity of extracellular histones in a subject, comprising administering an effective amount of a polyanion to the subject. In particular the invention relates to a method for the treatment of patients who are suffering from sepsis and employs polyanions to rapidly form complexes with and thus neutralize or inhibit the cytotoxic activity of extracellular histone proteins, for example, those found in the blood circulation of sepsis patients.

12 Claims, 13 Drawing Sheets

Ability of different sulfated oligosaccharides to protect HUVEC from histone cytotoxicity

HISTONE INHIBITION

CROSS-REFERENCE TO RELATED APPLICATIONS

The present application is a national stage application under 35 U.S.C. §371 of International Patent Application No. PCT/AU2011/001550, filed Nov. 29, 2011, which claims priority to U.S. Provisional Patent Application No. 61/418,826, filed Dec. 1, 2010.

TECHNICAL FIELD

The invention relates to the use of polyanions to inhibit the cytotoxic activity of histones. In addition the invention relates to the use of nanoparticle labelled histones to screen for polyanions which inhibit the cytotoxic activity of histones and the use of polyanions to inhibit the cytotoxic activity of histones in the treatment of sepsis.

BACKGROUND

Sepsis is a systemic inflammatory response to infection or trauma associated with and mediated by the activation of a number of host defense mechanisms including the cytokine network, leukocytes, and the complement and coagulation/fibrinolysis systems. Sepsis may be caused by bacterial, fungal, viral and other infections as well as by non-infective stimuli such as multiple trauma, severe burns, and organ transplantation. Within hours or days sepsis can progress to spontaneous clotting in the blood vessels, severe hypotension, multiple organ failure, and death.

Despite the clinical use of modern antibiotics, there remains a significant level of mortality due to ineffective treatment of patients with sepsis. Patients who are immunocompromised due to e.g. prophylaxis against graft rejection are also at increased risk. More leukemia patients die from sepsis than from their leukemia. It is estimated that there are 500 000 episodes of sepsis per year in the USA with a 35% crude mortality rate and 200 000 episodes of septic shock with a 40-70% mortality rate. Sepsis is the leading cause of death in non-coronary intensive care units. 40% of hospital deaths after injury are due to multiple organ dysfunction syndrome caused by sepsis.

Several attempts have been made in recent times to find an effective new therapy for sepsis patients. Considerable effort has been made to produce monoclonal antibodies against key mediators of inflammation, e.g. anti-tumour necrosis factor monoclonal antibodies, but these have proved clinically ineffective and have also been found to have dangerous side effects in sepsis patients. Another approach has been to use purified human coagulation factors, such as activated protein C (APC) including recombinant human APC (e.g. Xigris®). However, these APC based sepsis therapies have had little clinical impact. There are a number of reasons for this which include the anti-coagulant activity of APC which leads to an increased risk of haemorrhage thus the drug is excluded for sepsis which develops in patients post surgery or post trauma. For the same reason APC based sepsis therapeutics are excluded for leukemia patients who are at high risk of bleeding. Sepsis can progress rapidly and the relatively slow mode of action of APC based sepsis therapeutics is a disadvantage relative to the rapid progression of acute sepsis. Xigris was withdrawn from sale on Oct. 25, 2011.

Histones are small basic proteins that function in the cell nucleus to regulate gene expression and complex with DNA to form nucleosomes which assemble into chromatin structure. Xu et al, (Nat. Med. 2009. 15:1318-21) have reported a cytotoxic activity for histones released in response to inflammatory processes with the extracellular histones acting as mediators of endothelial cell dysfunction, organ failure and death in sepsis.

The present invention is predicated on the finding that polyanions can complex with extracellular histones in the circulation of a living animal and inhibit their cytotoxic activity. In addition the polyanions can complex with extracellular histones and prevent histone accumulation in organs. Further, these polyanions may have insignificant anticoagulant properties.

SUMMARY

The present inventors have identified that the cytotoxic activity of extracellular histones and extracellular histone accumulation in an organ can be inhibited by the administration of an oligosaccharide polyanion. The administration of an oligosaccharide polyanion offers a means of ameliorating at least some of the deficiencies of currently available sepsis treatments. Further, the use of a nanoparticle labelled histone provides a means for screening for compounds capable of inhibiting histone accumulation in organs.

In a first aspect there is provided a method of inhibiting the cytotoxic activity of extracellular histones in a subject, said method comprising administering an effective amount of a polyanion to said subject.

In a second aspect there is provided a method of inhibiting extracellular histone accumulation in a subject, said method comprising administering an effective amount of a polyanion to said subject.

In a third aspect there is provided a method of treating sepsis by inhibiting the cytotoxic activity of extracellular histones in a subject, said method comprising administering an effective amount of a polyanion to said subject.

In a fourth aspect there is provided the use of an effective amount of a polyanion for the manufacture of a medicament for the treatment of sepsis by inhibiting the cytotoxic activity of extracellular histones.

In a fifth aspect there is provided an effective amount of a polyanion for use in the treatment of sepsis.

In one embodiment the polyanion does not have substantial anticoagulant activity.

In one embodiment the polyanion may be substantially non-immunogenic.

In one embodiment the polyanion may be a polyanionic oligosaccharide having the general structure (I):

$$A\text{-}(B)_n\text{-}D \qquad (I)$$

wherein A and B are each independently a cyclic monosaccharide or a cyclic deoxy monosaccharide;

D is a cyclic monosaccharide, a cyclic deoxy monosaccharide, a ring-opened monosaccharide, or a sugar alcohol;

n is an integer selected from 0, 1, 2, 3, 4, 5, 6, 7 and 8; and wherein each of the cyclic monosaccharide, the cyclic deoxy monosaccharide, the ring-opened monosaccharide, or the sugar alcohol is independently optionally substituted with $OSO_3^-$, $COO^-$, $OPO_3^-$, an optionally substituted alkyl, an optionally substituted alkenyl, an optionally substituted alkynyl, an optionally substituted aryl, or an optionally substituted aralkyl; and wherein the polyanionic oligosaccharide includes at least two anionic substitutents selected from the group consisting of $OSO_3^-$, $COO^-$, and $OPO_3^-$.

In one embodiment the cyclic monosaccharide is selected from the group consisting of glucose, galactose, fructose, ribose, arabinose, xylose, lyxose, allose, altrose, mannose, gulose, idose, talose, ribulose, xylulose, psicose, sorbose, tagatose and sedoheptulose.

In another embodiment the cyclic monosaccharide is selected from the group consisting of glucose, galactose and fructose.

In another embodiment the cyclic deoxy monosaccharide is selected from the group consisting of fucose, deoxyribose and rhamnose.

In another embodiment the sugar alcohol is selected from the group consisting of glycerol, erythritol, threitol, ribitol, arabitol, xylitol, sorbitol (glucitol), mannitol, dulcitol (galactitol), iditol and fucitol.

In another embodiment the ring-opened monosaccharide is selected from the group consisting of glucose, galactose, fructose, erythrose, threose, erythrulose, ribose, arabinose, xylose, lyxose, allose, altrose, mannose, gulose, idose, talose, ribulose, xylulose, psicose, sorbose, tagatose and sedoheptulose.

In another embodiment the polyanion may be a polyanionic oligosaccharide having the general structure (I-a):

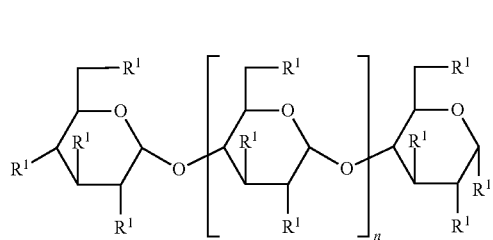

(I-a)

wherein each $R^1$ is independently selected from $OSO_3^-$, $COO^-$, $OPO_3^-$, $OH$ or $H$; and n is an integer between 0, 1, 2, 3, 4, 5, 6, 7, and 8; and wherein at least two of $R^1$ are selected from the group consisting of $OSO_3^-$, $COO^-$, and $OPO_3^-$.

In another embodiment the polyanion may be a polyanionic oligosaccharide having the general structure (I-b):

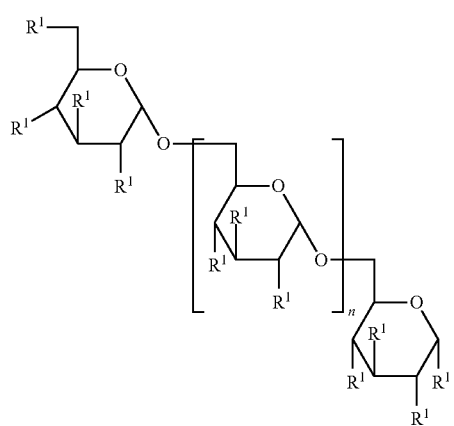

(I-b)

where each $R^1$ is independently selected from $OSO_3^-$, $COO^-$, $OPO_3^-$, $OH$ or $H$; and n is an integer between 0, 1, 2, 3, 4, 5, 6, 7, and 8; and wherein at least two of $R^1$ are selected from the group consisting of $OSO_3^-$, $COO^-$, and $OPO_3^-$.

In another embodiment the polyanion may be a polyanionic oligosaccharide selected from the group consisting of

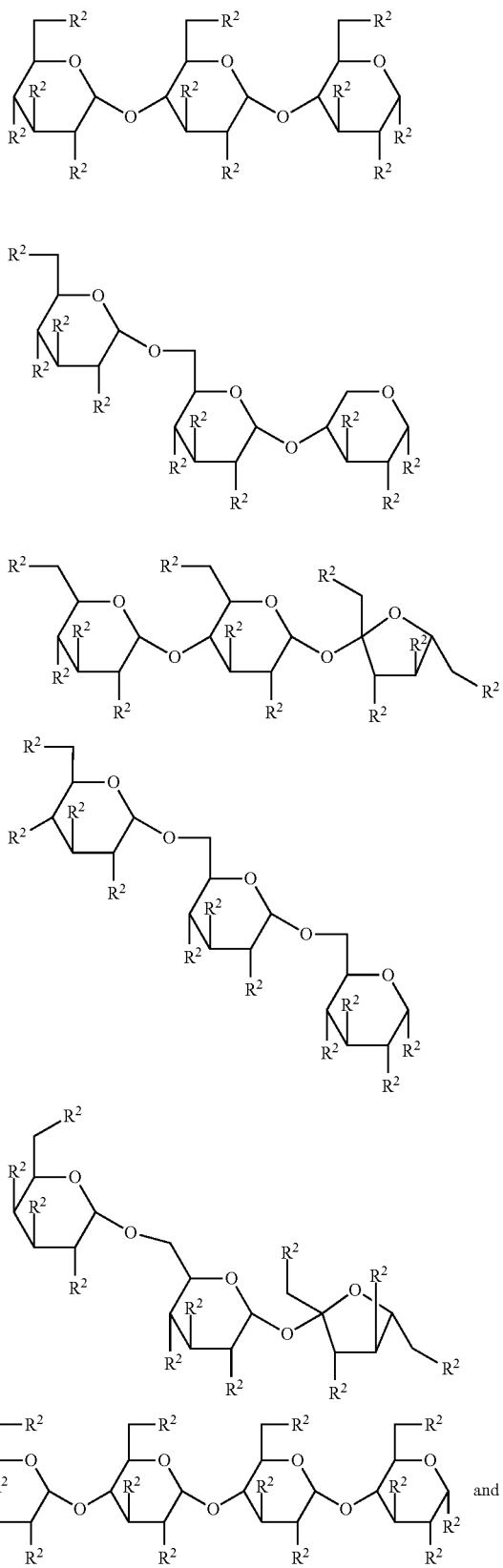

and

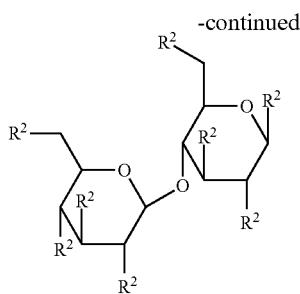

wherein each $R^2$ is independently selected from $OSO_3^-$, $COO^-$, $OPO_3^-$, OH or H; and wherein at least two of $R^2$ are selected from the group consisting of $OSO_3^-$, $COO^-$, and $OPO_3^-$.

In another embodiment the polyanion may be a polyanionic oligosaccharide selected from the group consisting of maltose sulfate, maltotriose sulfate, maltotetraose sulfate, maltopentaose sulfate, maltohexaose sulfate, maltoheptaose sulfate, maltooctaose sulfate, maltononaose sulfate and maltodecaose sulfate, panose sulfate, isomaltotriose sulfate, erlose sulfate, cellobiose sulfate and raffinose sulfate.

In a further embodiment the polyanion may be the polyanionic oligosaccharide cellobiose sulfate.

In one embodiment the polyanion may be a polyanionic cyclodextrin having the general structure (II):

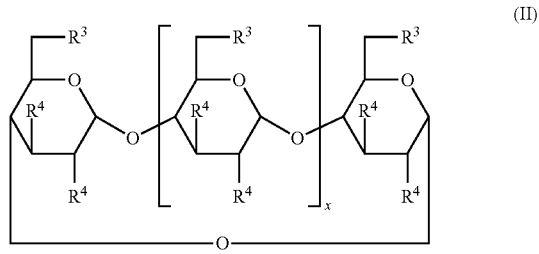

(II)

where each $R^3$ is independently selected from an optionally substituted O-alkyl, O-aryl, O-aralkyl, O-alkenyl, O-alkynyl group, $OSO_3^-$, $COO^-$, $OPO_3^-$, OH or H and each $R^4$ is independently selected from $OSO_3^-$, $COO^-$, $OPO_3^-$, OH or H; x is an integer between 3, 4, 5, 6, 7, 8, 9, and 10, and wherein the polyanionic cyclodextrin includes at least two anionic substitutents selected from the group consisting of $OSO_3^-$, $COO^-$ and $OPO_3^-$.

The cyclodextrin may be α-cyclodextrin, β-cyclodextrin or γ-cyclodextrin.

In another embodiment there is provided a method of screening for a histone inhibitor, said method comprising:
(i) contacting a histone with a candidate compound
(ii) determining binding of said candidate compound to said histone
(iii) selecting said candidate compound that binds said histone.

In another embodiment there is provided a method of screening for a histone is inhibitor, said method comprising:
(i) providing a nanoparticle labelled histone
(ii) administering said labelled histone to a test subject
(iii) administering a candidate compound to said test subject
(iv) monitoring histone localisation in an organ relative to a control subject
(v) selecting said candidate compound that alters histone localisation in an organ relative to a control subject.

In one embodiment the labelled histone may be administered to the test subject before, after or at the same time as the test compound.

In a further embodiment there is provided a method of screening for a histone inhibitor, said method comprising:
(i) providing a nanoparticle labelled histone
(ii) contacting said nanoparticle labelled histone with a candidate compound
(iii) administering said labelled histone and said test compound to a test subject
(iv) monitoring histone localisation in an organ of said test subject relative to a control subject.
(v) selecting said candidate compound that alters histone localisation in an organ relative to a control subject.

In one embodiment the candidate compound is a polyanion.

In one embodiment of any one of the preceding aspects the polyanion inhibits binding of a histone to a cell, tissue or organ.

BRIEF DESCRIPTION OF THE DRAWINGS

A preferred embodiment of the present invention will now be described, by way of an example only, with reference to the accompanying drawings wherein.

DEFINITIONS

Figure 1:
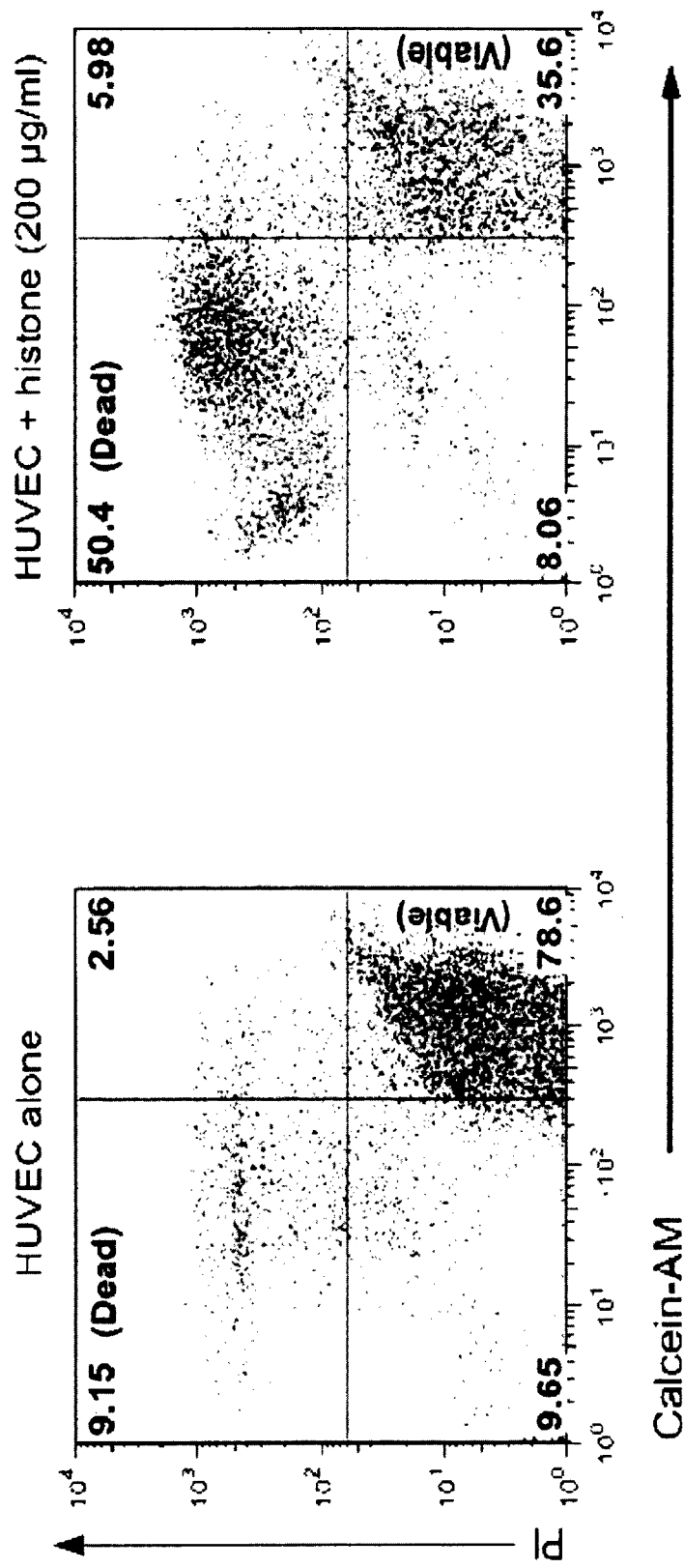
FIG. 1 depicts an example of data generated using the flow cytometry assay for histone cytotoxicity, in this case human umbilical vein endothelial cells (HUVEC) being incubated alone (left hand panel) or with 200 μg/ml of calf thymus histones (right hand is panel) for 1 hr in vitro. Figures in each panel represent the percentage of HUVEC in each quadrant, with viable (Calcein-AM-bright, PI-dull) and dead (Calcein-AM-dull, PI-bright) cell quadrants indicated.

Certain terms are used herein which shall have the meanings set forth as follows.

As used herein, the term "comprising" means "including principally, but not necessarily solely". Furthermore, variations of the word "comprising", such as "comprise" and "comprises", have correspondingly varied meanings.

Unless the context requires otherwise or specifically stated to the contrary, integers, steps, or elements of the invention recited herein as singular integers, steps or elements clearly encompass both singular and plural forms of the recited integers, steps or elements.

As used herein the terms "treating" and "treatment" refer to any and all uses which remedy a condition or symptoms, prevent the establishment of a condition or disease, or otherwise prevent, hinder, retard, or reverse the progression of a condition or disease or other undesirable symptoms in any way whatsoever.

It is to be noted that reference herein to use in therapeutic applications will be understood to be equally applicable to human and non-human, such as veterinary, applications. Hence it will be understood that, except where otherwise indicated, reference to a patient, subject or individual means a human or non-human, such as an individual of any species of social, economic or research importance including but not limited to avian, lagomorph, ovine, bovine, equine, porcine, feline, canine, primate and rodent species.

In the context of this specification the term "effective amount" includes within its meaning a sufficient but non-toxic amount of a compound or composition of the invention to provide the desired effect. The exact amount required will vary from subject to subject depending on factors such as the desired effect, the species being treated, the age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

As used herein the term "monosaccharide" includes within its meaning a sugar or carbohydrate of general formula $C_nH_{2n}O_n$. For example, the term monosaccharide includes, but is not limited to, glucose, galactose, fructose, erythrose, threose, erythrulose, ribose, arabinose, xylose, lyxose, allose, altrose, mannose, gulose, idose, talose, ribulose, xylulose, psicose, sorbose, tagatose and sedoheptulose. Monosaccharides can be both naturally occurring or synthetic. Most monosaccharides exist as either a ring-opened monosaccharide or a cyclic monosaccharide.

As used herein the term "deoxy monosaccharide" or "deoxy sugar" includes within its meaning a sugar containing fewer oxygen atoms than carbon atoms, resulting in one or more carbons in the molecule lacking an attached hydroxyl group. For example, the term deoxy monosaccharide includes, but is not limited to, fucose, deoxyribose and rhamnose.

As used herein the term "sugar alcohol" includes within its meaning a hydrogenated form of carbohydrate or monosaccharide, whose carbonyl group (aldehyde or ketone) has been reduced to a primary or secondary hydroxyl group (hence the alcohol). Sugar alcohols have the general formula $H(HCHO)_{n+1}H$. For example, the term sugar alcohol includes, but is not limited to, glycol, glycerol, erythritol, threitol, ribitol, arabitol, xylitol, sorbitol (glucitol), mannitol, dulcitol (galactitol), iditol and fucitol.

As used herein the term "oligosaccharide" includes within its meaning carbohydrates that are composed of two to ten monosaccharide residues joined through glycosidic linkage, which can be hydrolyzed by acid to give the constituent monosaccharide units.

As used herein the term "polysaccharide" includes within its meaning polymers of monosaccharides containing ten or more monosaccharide residues joined through glycosidic linkage, which can be hydrolyzed by acid to give the constituent monosaccharide units.

As used herein, the term "alkyl" includes within its meaning monovalent straight chain or branched chain saturated hydrocarbon radicals having from 1 to 18 carbon atoms, e.g., 1, 2, 3, 4, 5, 6, 7, 8, 9, 10, 11, 12, 13, 14, 15, 16, 17 or 18 carbon atoms. For example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, 2-ethylpentyl, 3-ethylpentyl, heptyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3-trimethylbutyl, 1,1,2-trimethylbutyl, 1,1,3-trimethylbutyl, 5-methylheptyl, 1-methylheptyl, octyl, nonyl, decyl, undecyl, dodecyl, triskaidecyl, tetradecyl, quindecyl, hexadecyl, heptadecyl, octadecyl and the like.

As used herein the term "alkylene" includes within its meaning divalent, saturated, straight chain hydrocarbon radicals.

As used herein, the term "aryl" includes within its meaning monovalent, single, polynuclear, conjugated and fused aromatic hydrocarbon radicals, for example phenyl, naphthyl, anthracenyl, pyrenyl, phenanthracenyl.

As used herein the term "arylene" includes within its meaning divalent, single, polynuclear, conjugated and fused aromatic hydrocarbon radicals.

As used herein, the term "aralkyl" includes within its meaning a lower-alkyl residue substituted by one or more aryl or substituted aryl groups, such as, for example, benzyl, phenyl methyl, phenylethyl, phenylpropyl, phenylisopropyl, phenyl-tertiary butyl, and the like.

The term "alkenyl" refers to a hydrocarbon radical having at least one carbon-carbon double bond. A $C_2$-$C_6$ alkenyl group is an alkenyl group having from two to six carbon atoms in straight or branched alkenyl backbone. Exemplary alkenyl radicals include, without limitation, vinyl, propenyl, 2-butenyl, and the like. An alkenyl group may be substituted with one or moieties as described for alkyl groups.

The term "alkynyl", as used herein, refers to a hydrocarbon radical having at least one carbon-carbon triple bond. A $C_2$-$C_6$ alkynyl group is an alkynyl group having from two to six carbon atoms in straight or branched alkynyl backbone. Exemplary alkynyl moieties include propynyl, 3-hexynyl, and the like. An alkynyl group may be substituted with one or moieties as described for alkyl groups.

As used herein the term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, nitrogen containing groups such as $NO_2$, $NO_3^-$, $N(alkyl)_2$, $NH(alkyl)$, nitroalkyl, nitroalkenyl, nitroalkynyl, nitroheterocyclyl, alkylamino, dialkylamino, alkenylamine and alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkyl carbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, sulphur containing groups such as $SO_3H$, $SO_3^-$, $OSO_3^-$, $SO_3alkyl$, $SO_3aryl$, $NHSO_3H$, and $NHSO_3^-$, $CO_2H$, $COO^-$, $CO_2alkyl$, $C(O)NH_2$, —$C(O)NH(alkyl)$, and —$C(O)N(alkyl)_2$. Preferred substituents include $C_{1-10}$ alkyl, $C_{1-10}$ alkoxy, —$CH_2$—($C_{1-10}$) alkoxy, $C_{6-10}$ aryl, e.g., phenyl, —$CH_2$-phenyl, halo, hydroxyl, hydroxy($C_{1-10}$)alkyl, and halo-($C_{1-10}$)alkyl, e.g., $CF_3$, $CH_2CF_3$. Particularly preferred substituents include $C_{1-10}$ alkyl, $C_{1-10}$ alkoxy, halo, hydroxyl, hydroxy($C_1$-$C_{10}$) alkyl, e.g., $CH_2OH$, and halo-($C_{1-10}$)alkyl, e.g., $CF_3$, $CH_2CF_3$.

As used herein the term "sepsis" includes within its meaning all stages of the disease or condition as characterised by standard medical reference texts and/or known to one of skill in the art. For example sepsis includes severe sepsis, acute and chronic sepsis and septic shock. Sepsis also includes sepsis episodes associated with burns patients, therapeutic regimes for cancer patients, perinatal complications in maternity patients, immunosuppressive prophylaxis for graft recipients, and post-operative surgical patients.

As used herein, the term "nanoparticle" refers to any solid particulate of less than, 1 micron (1000 nm) diameter. In particular, a nanoparticle may be a FibrinLite nanoparticle is consisting of metallic platelets of technetium-99m radionuclide encapsulated by a plurality of layers of graphitic carbon. The diameter of FibrinLite nanoparticles is log-normal distributed over the range 20-400 nm with a median diameter of approximately 200 nm.

DETAILED DESCRIPTION

This invention relates to a method for the treatment of patients who are suffering from sepsis due to infection, and employs polyanions to rapidly form complexes with and thus neutralise or inhibit the cytotoxic activity of extracellular histone proteins, for example, those found in the blood circulation of sepsis patients. In addition the polyanions can complex extracellular histones and prevent histone accumulation in organs, in particular the lungs. In preferred embodiments the polyanions are selected for their low interference with blood coagulation and haemostasis and/or their ability to persist in the circulation.

The present invention is predicated on the finding that oligosaccharide polyanions that may have insignificant anticoagulant properties can complex with histones in the circulation of a living animal and prevent histone binding to organs. These polyanions provide a new means of therapeutic intervention in sepsis and provide more attractive alternatives to the use of neutralising antibodies, APC or heparin.

Sepsis

Sepsis is a systemic reaction characterized by arterial hypotension, metabolic acidosis, decreased systemic vascular resistance, tachypnea and organ dysfunction. Sepsis (including septic shock) is a systemic inflammatory response to infection or trauma, associated with and mediated by the activation of a number of host defense mechanisms including the cytokine network, leukocytes, and the complement and coagulation/fibrinolysis systems. Disseminated intravascular coagulation (DIC) with widespread deposition of fibrin in the microvasculature of various organs may be an early manifestation of sepsis. DIC is an important mediator in the development of the multiple organ failure syndrome and contributes to the poor prognosis of patients with septic shock.

Sepsis may develop from organisms, their metabolic products or toxins in the blood stream. That is, sepsis encompasses bacteremia, fungemia, viremia, and parasitemia. Thus, septic shock (acute circulatory failure resulting from sepsis often associated with is multiple organ failure and a high mortality rate) may be caused by a number of organisms or disease processes. Sepsis may also be caused by non-infective stimuli such as trauma, severe burns, intestinal torsion, amniotic fluid embolism and organ transplantation.

Many patients with sepsis exhibit a rapid decline over a 24-48 hour period. Thus, rapid treatment is essential for effective sepsis treatment. Unfortunately diagnosis of type of infection requires microbiological analysis to identify the pathogen which may take a number of days. Therefore therapy to eliminate a pathogen (e.g. antibiotic therapy) must be initiated without knowledge of the type and species of the pathogen, and with no means of knowing the extent of the infection.

Several attempts have been made to find an effective new therapy for sepsis patients such as monoclonal antibodies against key mediators of inflammation and activated protein C (APC). However, these treatments have had little clinical impact, and APC has recently been withdrawn from the market. Low-dose heparin has been used in the treatment of sepsis patients although its use in this setting is complicated and controversial due to the well-recognized increased risk of bleeding in sepsis patients due to lower platelet counts and/or depleted clotting factors, especially when the sepsis has induced disseminated intravascular coagulation (DIC). Depletion of platelets and/or clotting factors by low-dose heparin may then lead to clotting dysfunction and catastrophic haemorrhage may occur. Heparin may also induce in some patients a condition known as heparin-induced thrombocytopaenia (HIT), wherein antibody-mediated destruction of platelets can also lead to dangerous haemorrhage.

Histones

Histones are small, basic proteins with high a content of lysine or arginine and function in the packaging of DNA. Histones are highly conserved and can be grouped into five major classes: H1/H5, H2A, $H_2B$, H3, and H4 organised into two super-classes of the core histones (H2A, $H_2B$, H3 and H4) and the linker histones (H1 and H5).

Two of each core histone assemble to form octameric nucleosome core particles by wrapping DNA around the protein complex. Linker histones bind the nucleosome and the DNA where it enters and exits the nucleosome thereby locking the DNA in place and facilitating formation of higher order structure.

As described herein a histone may be a full length histone, a fragment or variant thereof. A histone variant may be modified by, for example, the deletion, addition and/or substitution of amino acid(s). Alternatively, a histone may be modified by acetylation and/or methylation of lysine and arginine. In general, the modifications do not substantially compromise the polycationic nature of the histone or the ability of the is histone to localise in an organ.

Suitable amino acid substitutions include, but are not necessarily limited to, amino acid substitutions known in the art as "conservative". A "conservative" substitution is one in which an amino acid is substituted for another amino acid that has similar properties, such that one skilled in the art of peptide chemistry would expect the biological activity, secondary structure and/or hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine, histidine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A histone variant may also, or alternatively, contain non-conservative amino acid changes.

In certain embodiments, a histone variant may be modified by the deletion, addition and/or substitution of amino acid(s) and differ from the unmodified sequence by substitution, deletion or addition of five amino acids or fewer, such as by four, or three, or two, or one amino acid(s).

As used herein a histone "variant" refers to a histone with a substantially similar sequence to the naturally occurring histone sequence. In general, two sequences are "substantially similar" if the two sequences have a specified percentage of amino acid residues that are the same (percentage of "sequence identity"). Accordingly, a "variant" of a histone sequence may share at least about 40%, 45%, 50%, 55%, 60%, 65%, 70%, 75%, 80%, 83% 85%, 88%, 90%, 93%, 95%, 96%, 97%, 98% or 99% sequence identity with a reference histone sequence.

In general, histone sequence variants possess qualitative biological activity in common. Also included within the meaning of the term "variant" are homologues of histones. A histone homologue is typically from a different species but sharing substantially the same biological function or activity as the corresponding histone from another species. For example, homologues of histones include but are not limited to, those from different species of mammals or microorganisms.

Further, the term "variant" also includes analogues of histone sequences. A histone "analogue" is a polypeptide which is a derivative of a given histone, which derivative comprises addition, deletion, substitution of one or more amino acids, such that the polypeptide retains substantially the same function. As noted above, the term "conservative amino acid substitution" refers to a substitution or replacement of one amino acid for another amino acid with similar properties within a histone sequence.

In certain embodiments, a "variant" of a histone differs in sequence (from the related histone) by substitution, deletion or addition of five amino acids or fewer, such as by four, or three, or two, or one amino acid(s).

Also included within the scope of the invention are fragments of histones. A histone "fragment" is a polypeptide that is a constituent of a histone or a variant thereof. Typically the fragment possesses qualitative biological activity in common with the histone of which it is a constituent. Typically, the histone fragment may be greater than 50 amino acids in length, between about 5 and about 50 amino acid residues in length, between about 5 and about 45 amino acid residues in length, between about 5 and about 40 amino acid residues in length, between about 5 and about 35 amino acid residues in length, between about 5 and about 30 amino acid residues in length, between about 5 and about 25 amino acid residues in length, between about 5 and about 20 amino acid residues in length, between about 5 and about 15 amino acid residues in length, or between about 5 and about 10 amino acid residues in length. In certain embodiments, a fragment of a polypeptide of the invention is 6, 7, 8, 9, 10, 11, 12, 13, 14, 15, 16, 17, 18, 19, 20, 21, 22, 23, 24, 25, or more than 25 amino acid residues in length.

Polyanions

The inventors propose that as histones are polycations with a high isoelectric point, they will form complexes with polyanions other than DNA, such as sulfated polyanionic polysaccharides, (e.g. heparin), polyanionic oligosaccharides and disaccharides, linear polyanions, cyclitol polyanions, and arylene urea polyanions.

In some embodiments the polyanion can complex with and thus inhibit the biological activity of circulating histones without any impact on the coagulation system. This would provide the treating physician with the option of a wider dose range of a polyanion that could be utilized completely independent of the platelet count and to coagulation status of the sepsis patient, even when DIC is present, without and still not promote bleeding. These polyanions should also not promote destruction of platelets.

In preferred embodiments the polyanion is stable and is not rapidly degraded in vivo. Further, polyanions as described herein may be stable at room temperature and thus be stored for long periods without substantial degradation.

Polyanionic Polysaccharides

Heparin is a naturally occurring sulfated polysaccharide extensively used in clinical medicine as an anti-coagulant. Its anti-coagulant activity can be controlled or even neutralised in patients by administration of a pharmaceutically acceptable polycation such as protamine.

It is proposed that heparin, a polyanion, would complex with circulating polycationic histones and therefore be beneficial for sepsis patients in a dose sufficient to complex with circulating histones but insufficient to have an apparent anticoagulant effect. Other polyanionic polysaccharides known to those skilled in the art, such as heparan sulfate including the proteoglycans perlecan and syndecan, chondroitin sulfate; dermatan sulfate; pentosan polysulfate (Elmiron), sulodexide (HS/DS), oversulfated hyaluronic acid, fucoidan and oversulfated chondroitin sulfate (Arteparon®) may also be used at dosages that are sufficient to complex with circulating histones but are insufficient to have an appreciable anticoagulant effect.

In other embodiments the polyanionic polysaccharide may be a partially de-sulfated heparin which has been chemically modified to remove some of the sulfate groups, a low molecular weight heparin, or a chemically modified heparin (eg periodate treated, glycol split heparin) that lacks significant anti-coagulant activity but maintains the ability to rapidly complex efficiently with histones. In some embodiments the polyanionic polysaccharide may be selected from the group consisting of N-acetylated heparin, glycol split heparin, glycol split N-acetylated heparin, enoxaparin, glycol split enoxaparin and glycol split low molecular weight heparin (3 KDa).

Polyanionic Oligosaccharides

In one embodiment the polyanion is a polyanionic oligosaccharide having the general structure (I):

A-(B)$_n$-D  (I)

wherein A and B are each independently a cyclic monosaccharide or a cyclic deoxy to monosaccharide;

D is a cyclic monosaccharide, a cyclic deoxy monosaccharide, a ring-opened monosaccharide, or a sugar alcohol;

n is an integer selected from 0, 1, 2, 3, 4, 5, 6, 7 and 8; and wherein each of the cyclic monosaccharides, the cyclic deoxy monosaccharide, the ring-opened monosaccharide, or the sugar alcohol is independently optionally substituted with OSO$_3^-$, COO$^-$, OPO$_3^-$, an optionally substituted alkyl, an optionally substituted alkenyl, an optionally substituted alkynyl, an optionally substituted aryl, or an optionally substituted aralkyl; and wherein the polyanionic oligosaccharide includes at least two anionic substituents selected from the group consisting of OSO$_3^-$, COO$^-$, and OPO$_3^-$.

In one embodiment the cyclic monosaccharide is selected from the group consisting of glucose, galactose, fructose, ribose, arabinose, xylose, lyxose, allose, altrose, mannose, gulose, idose, talose, ribulose, xylulose, psicose, sorbose, tagatose and sedoheptulose. In another embodiment the cyclic monosaccharide is selected from the group consisting of glucose, galactose and fructose.

In one embodiment the cyclic deoxy monosaccharide is selected from the group consisting of fucose, deoxyribose and rhamnose.

In one embodiment the sugar alcohol is selected from the group consisting of glycol, glycerol, erythritol, threitol, ribitol, arabitol, xylitol, sorbitol (glucitol), mannitol, dulcitol (galactitol), iditol and fucitol. In another embodiment the sugar alcohol is selected from the group consisting of sorbitol and dulcitol.

In one embodiment the ring-opened monosaccharide is selected from the group consisting of glucose, galactose, fructose, erythrose, threose, erythrulose, ribose, arabinose, xylose, lyxose, allose, altrose, mannose, gulose, idose, talose, ribulose, xylulose, psicose, sorbose, tagatose and sedoheptulose.

In one embodiment the ring-opened monosaccharide can be reductively aminated with aryl or alkyl amines.

In one embodiment the cyclic monosaccharides are linked by a 1,1, 1,2, 1,3, 1,4, 1,5 or 1,6 linkage. In one embodiment the cyclic monosaccharides are linked by a 1,4 or 1,6 linkage. In one embodiment the cyclic monosaccharides are linked by an α bond. In another embodiment the cyclic monosaccharides are linked by a β bond. In a further embodiment, where more than 2 monosaccharides are present, each of the monosaccharides are linked by a bonds. In a further embodiment, where more than 2 monosaccharides are present, each of the monosaccharides are linked by β bonds. In another embodiment, where more than 2 monosaccharides are present, the monosaccharides are linked by a combination of α and β bonds.

In one embodiment, A, B and D are each a cyclic monosaccharide selected from the group consisting of glucose, galactose and fructose, and each hydroxyl group of the glucose, galactose or fructose is optionally substituted with SO$_3^-$ or PO$_3^-$.

The polyanionic oligosaccharide may be selected from the group comprising maltose sulfate, maltotriose sulfate, maltotetraose sulfate, maltopentaose sulfate, maltohexaose sulfate, maltoheptaose sulfate, maltooctaose sulfate, maltononaose sulfate and maltodecaose sulfate, panose sulfate, isomaltotriose sulfate, erlose sulfate, cellobiose sulfate and raffinose sulfate.

In a further embodiment the polyanionic oligosaccharide may be cellobiose sulfate.

In another embodiment the polyanion may be a polyanionic oligosaccharide having the general structure (I-a):

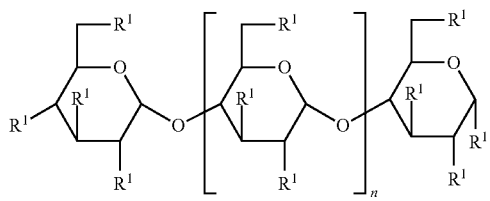

where each R$^1$ is independently selected from OSO$_3^-$, COO$^-$, OPO$_3^-$, OH or H; and n is an integer between 0, 1, 2, 3, 4, 5, 6, 7, and 8; and wherein at least two of R$^1$ are selected from the group consisting of OSO$_3^-$, COO$^-$, and OPO$_3^-$. In one embodiment n is 1, 2, 3 or 4. In another embodiment n is 1 or 2. In one embodiment each R$^1$ is OSO$_3^-$.

In another embodiment the polyanion may be a polyanionic oligosaccharide having the general structure (I-b):

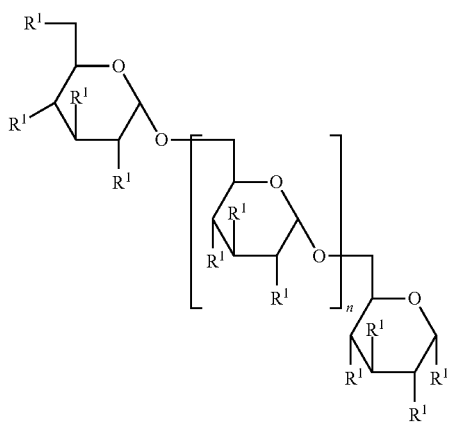
(I-b)

where each $R^1$ is independently selected from $OSO_3^-$, $COO^-$, $OPO_3^-$, OH or H; and n is an integer between 0, 1, 2, 3, 4, 5, 6, 7, and 8; and wherein at least two of $R^1$ are selected from the group consisting of $OSO_3^-$, $COO^-$, and $OPO_3^-$. In one embodiment n is 1, 2, 3 or 4. In another embodiment n is 1 or 2. In one embodiment each $R^1$ is $OSO_3^-$.

In another embodiment the polyanionic oligosaccharide may be selected from the following group:

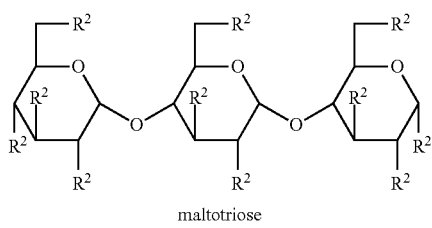
maltotriose

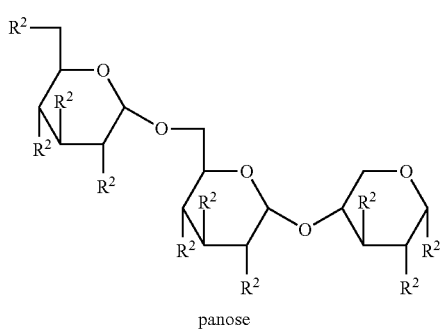
panose

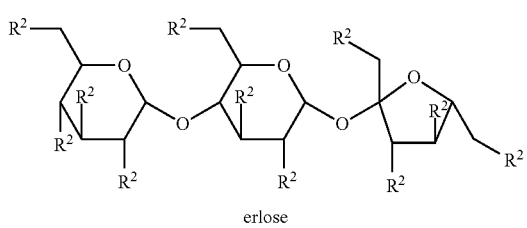
erlose

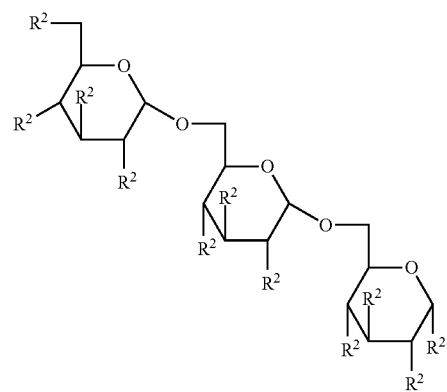
isomaltotriose

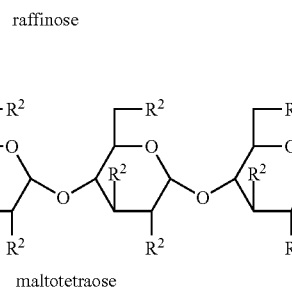
raffinose

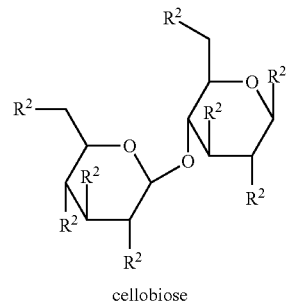
maltotetraose cellobiose where each $R^2$ is independently selected from $OSO_3^-$, $COO^-$, $OPO_3^-$, OH or H; and wherein at least two of $R^2$ are selected from the group consisting of $OSO_3^-$, $COO^-$, and $OPO_3^-$.

In a further embodiment the polyanion may be a polyanionic cyclodextrin having the general structure (II):

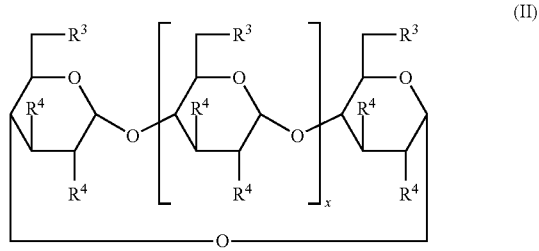

(II)

where each $R^3$ is independently selected from an optionally substituted O-alkyl, O-aryl, O-aralkyl, O-alkenyl, O-alkynyl group, $OSO_3^-$, $COO^-$, $OPO_3^-$, OH or H and each $R^4$ is independently selected from $OSO_3^-$, $COO^-$, $OPO_3^-$, OH or H; x is an integer between 3, 4, 5, 6, 7, 8, 9, and 10 and wherein the polyanionic cyclodextrin includes at least two anionic substituents selected from the group consisting of $OSO_3^-$, $COO^-$, and $OPO_3^-$.

In one embodiment x is 4, 5 or 6. The cyclodextrin may be α-cyclodextrin, β-cyclodextrin or γ-cyclodextrin.

In another embodiment the oligosaccharide is a sulfated oligosaccharide or a ring-opened oligosaccharide.

In other embodiments the polyanion may be a sulfated open ring form of the reducing sugar end of a trisaccharide or tetrasaccharide such as sulfated maltotriitol and maltotetraitol respectively. Derivatives of those trisaccharides or tetrasaccharides may be reductively aminated moieties with alkyl and aryl groups, either maintaining or opening the ring of the reducing sugar.

In another embodiment, the polyanion is a disaccharide, oligosaccharide, ring-opened disaccharide or ring-opened oligosaccharide having the following structural formula:

$E\text{-}(G)_a$ wherein a is an integer between 1 and 10; E is selected from the group consisting of: a diose, a triose, a tetraose, a pentose, a hexose, a heptose, an octose and a nonose, and each independent G is selected from the group consisting of: a diose, a triose, a tetraose, a pentose, a hexose, a heptose, an octose and a nonose;

wherein E and G, and where a is an integer of 2 or greater, G and G, linked via a group selected from: —O—$(CH_2)_x$—O—, —O—, —$OCH_2$—, —NH—, —S—, —$NR(CH_2)_x$—Ar—$(CH_2)_xNR_1$—, —$NR(CH_2)_xNR_1$—, —$O(CH_2)_x$—Ar—$(CH_2)_xO$—, —C(O)—$N(R_2)$—$(CH_2)_x$—$N(R_2)$—C(O)—, —$N(R_2)$—C(O)—Ar—$(CH_2)_x$—Ar—C(O)—$N(R_2)$— and —$N(R_2)$—$(CH_2)_x$—$N(R_2)$—; R, $R_1$ and $R_2$ are selected from the group consisting of: hydrogen, alkyl, aryl, heteroaryl and C(O)-alkyl;

x is an integer between 0 and 10;

wherein E and G may be substituted with a functional group selected from the group consisting of: alkyl, alkenyl, aryl, halo, heteroaryl, an amide derivative such as —NH-$COCH_3^-$, alkoxy such as —$OCH_3^-$, —O— and —OH;

and wherein said diose, triose, tetraose, pentose, hexose, heptose, octose and nonose may be sulfated, phosphorylated or carboxylated.

In an embodiment E and each G are independently selected from the group consisting of a pentose, a hexose and a heptose, and are linked via a group selected from: —O—$(CH_2)_x$—O—, —O—, —$OCH_2$—, —$NR(CH_2)_x$—Ar—$(CH_2)_xNR_1$—, —$O(CH_2)_x$—Ar—$(CH_2)_xO$—, —C(O)—N$(R_2)$—$(CH_2)_x$—$N(R_2)$—C(O)—, —$N(R_2)$—C(O)—Ar—$(CH_2)_x$—Ar—C(O)—$N(R_2)$—, and R, $R_1$ and $R_2$ are selected from the group consisting of: hydrogen, acetyl and alkyl, and x is an integer is between 1 and 6.

In another embodiment, the hexose may be selected from the group consisting of: glucose, galactose, mannose, fructose, fucose, and idose, and the pentose may be xylose.

Linear and Linked Polyanions

In other embodiments the polyanion may be a sulfated construct of 2 reductively linked sugars, through their reducing termini, thus having opened rings and presenting a linear polyol structure. For example the linker —$NH_2$—$CH_2$—CHOH—$CH_2$—$NH_2$— may link 2 reduced glucose or glucuronic acid units. The chain length and the number of potential sulfate groups per molecule in this type of structure can also be extended by appropriate choice of the type of sugar as the starting subunits, for example a heptose such as sedoheptulose instead of a hexose such as glucose. In other embodiments the polyanion may be a sulfated construct with a linker between cyclic monosaccharide and ring-opened monosaccharides.

In other embodiments the polyanion may be a polyanionic linear polyol of 12, 13, 13, 15, 16, 17, or 18 carbon atom chain length. The polyanionic linear polyol may contain unsaturated bonds, branched chains or ring structures that may be saturated or unsaturated. The polyanionic linear polyol can be optionally substituted. Alcoholic precursor examples are 1,2,13,14-tetradecan-tetraol, 5-(hydroxymethyl)undecane-1,5,6,7,11-pentol, octadecane-1,18-diol, and hydrolyzed squalene derivatives. In one embodiment the polyanionic linear polyol is sulfated. In other embodiments the polyanionic linear polyol includes at least 2 substituents selected from a sulfate group, a carboxylate group and a phosphate group.

In other embodiments the polyanion may be a polyanionic compound based on alkyl polyols or attached to aromatic rings for example, suramin and related derivatives.

Cyclitol Polyanions

In a further embodiment, the polyanion is a cyclitol having the following structural formula:

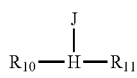

wherein:

H is selected from the group consisting of: N, CH, O, S, or a linker selected from —CO—NH—K—NH—CO—, —NH—CO—K—CO—NH—, —NH—K—NH—, —O—K—O—;

K is selected from the group consisting of alkylene and arylene;

$R_{10}$ is a 4-, 5-, or 6-membered carbocyclic ring that is saturated or unsaturated, wherein the ring comprises at least one sulfate group, at least one carboxylate group or at least one phosphate group.

$R_{11}$, is selected from the group consisting of a 4-, 5-, or 6-membered carbocyclic ring that is saturated or unsaturated, wherein the ring comprises at least one sulfate group, at least one carboxylate group or at least one phosphate group, hydrogen, aryl and alkyl;

J is selected from the group consisting of: hydrogen, alkyl, aryl, -L-C($R_{12}$)($R_{13}$) and acetate;

L is selected from the group consisting of: —(CH$_2$)$_x$—, —CH$_2$—Ar—CH$_2$—, —CH$_2$CH(OH)CH$_2$—, —(CH$_2$)$_x$—Ar—(CH$_2$)$_x$—, wherein the L group may optionally comprise one or more sulfate groups, one or more carboxylate groups or one or more phosphate groups.

$R_{12}$ and $R_{13}$ are independently selected from the group consisting of: 4-, 5-, or 6-membered carbocyclic ring that is saturated or unsaturated, hydrogen, aryl and alkyl, wherein $R_{12}$ and/or $R_{13}$ may comprise one or more sulfate groups, one or more carboxylate groups or one or more phosphate groups, and x is an integer between 0 and 10.

In one embodiment, L is selected from the group consisting of: —(CH$_2$)$_x$—, wherein x is an integer between 2 and 10, CH$_2$—Ar—CH$_2$ and CH$_2$CH(OSO$_3$H)CH$_2$.

In an alternative embodiment, $R_{10}$, $R_{11}$, $R_{12}$ and $R_{13}$ may be independently selected from the following:

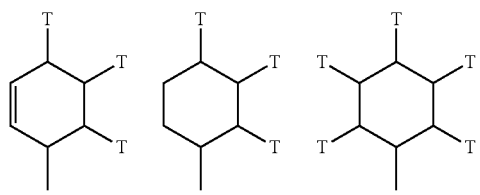

wherein T is independently selected from the group consisting of SO$_3$H, SO$_3^-$, COOH, COO$^-$, OPO$_3$H and OPO$_3^-$.

Arylene Urea Polyanions

In a further embodiment of the first aspect, the polyanion is an arylene urea of the following formula:

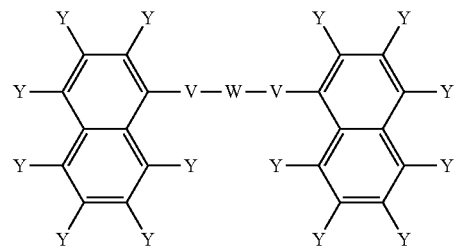

wherein each Y is independently selected from the group consisting of: SO$_3$H, SO$_3^-$, hydrogen, alkyl, halo, phenyl, an amide derivative, —NHCOCH$_3$, NO$_3^-$—O—, —OCH$_3$, is COOH, COO$^-$, OPO$_3$H and OPO$_3^-$.

each V is independently selected from the group consisting of: —(NHC(O)Ph)$_z$-, (CH$_2$)$_u$ and phenyl;

W is —NH—C(O)—NH—;

u and z may independently of each other be an integer between 0, 1, 2, 3, 4, 5, 6, 7, 8, 9 and 10.

In one embodiment, the arylene urea may be suramin, or a salt thereof.

Examples of polyanions useful in the methods and compositions of the invention include the following:

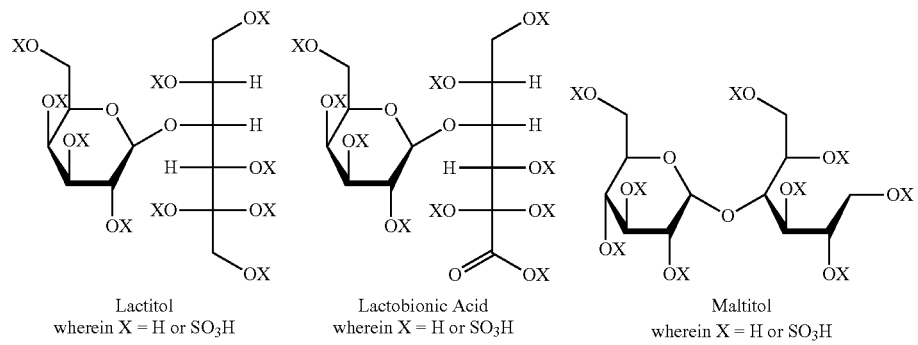

Lactitol
wherein X = H or SO$_3$H

Lactobionic Acid
wherein X = H or SO$_3$H

Maltitol
wherein X = H or SO$_3$H

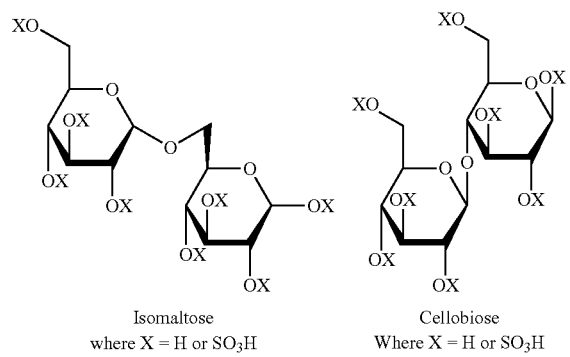

Isomaltose
where X = H or SO$_3$H

Cellobiose
Where X = H or SO$_3$H

-continued
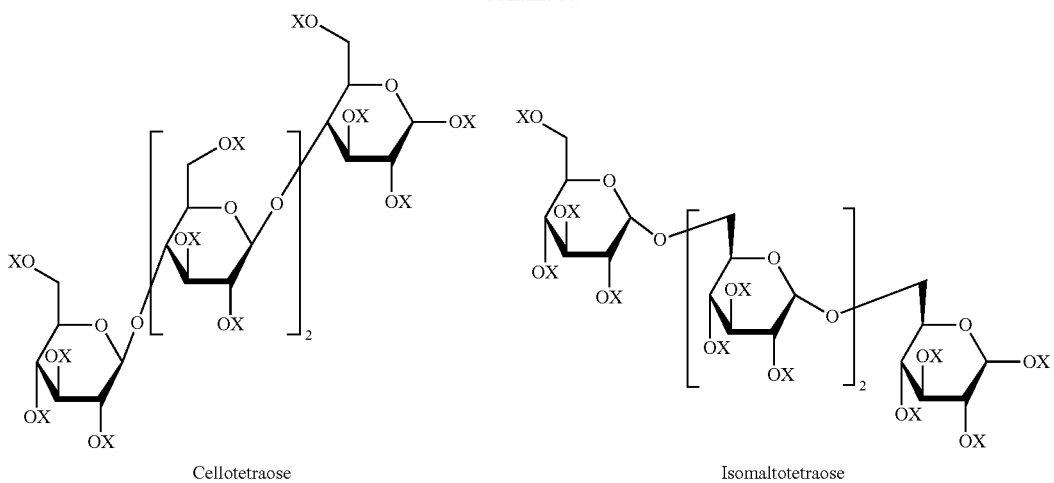
Cellotetraose
wherein X = H or SO₃H
Isomaltotetraose
where X = H or SO₃H
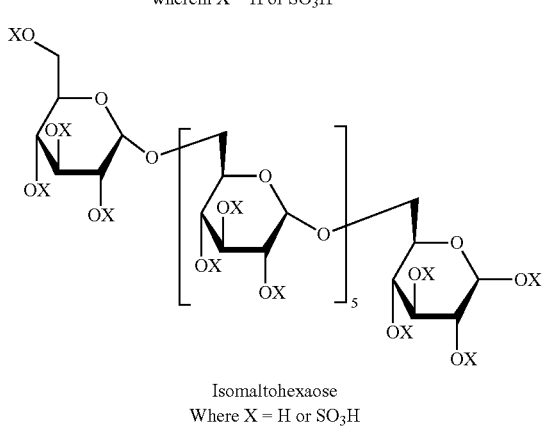
Isomaltohexaose
Where X = H or SO₃H
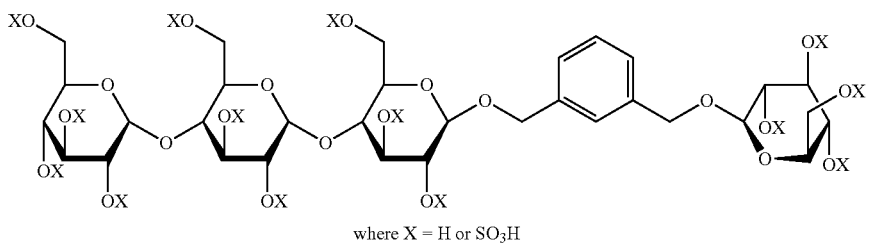
where X = H or SO₃H
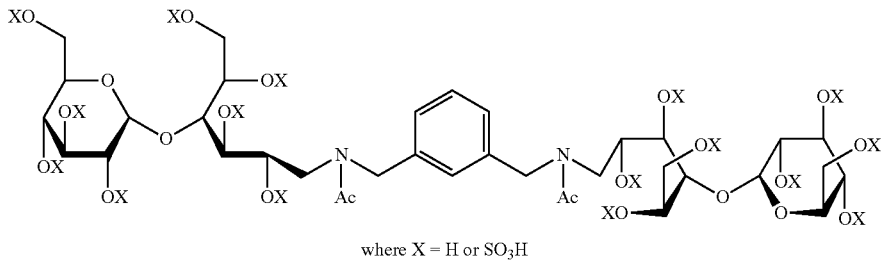
where X = H or SO₃H
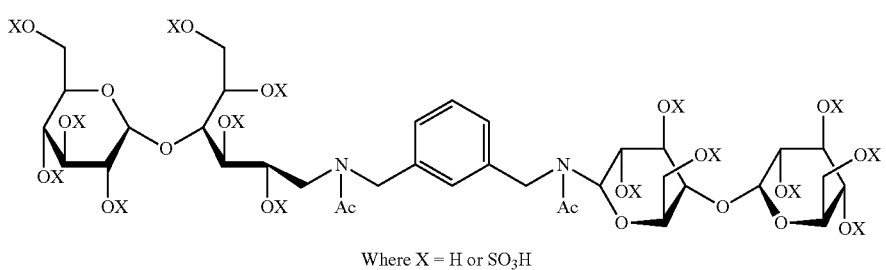
Where X = H or SO₃H

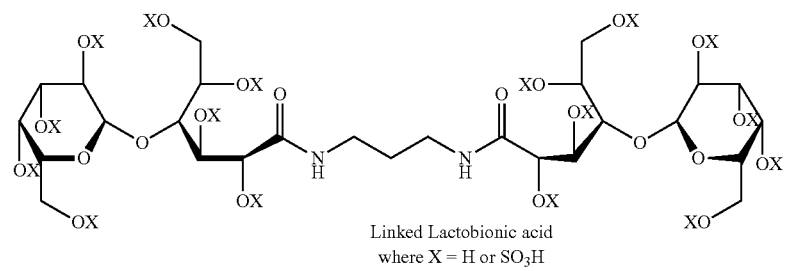
Linked Lactobionic acid
where X = H or SO₃H
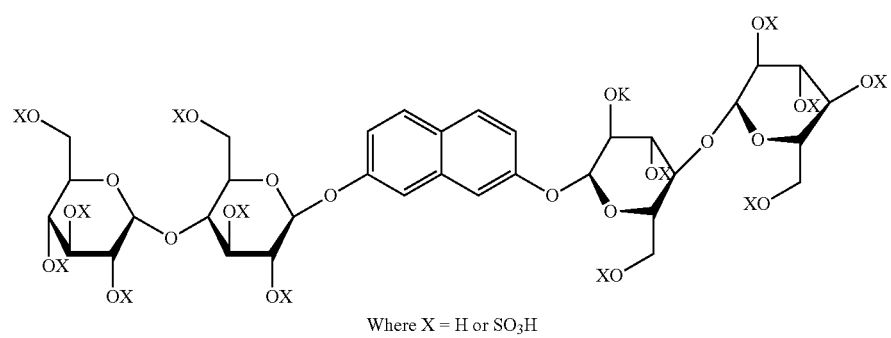
Where X = H or SO₃H
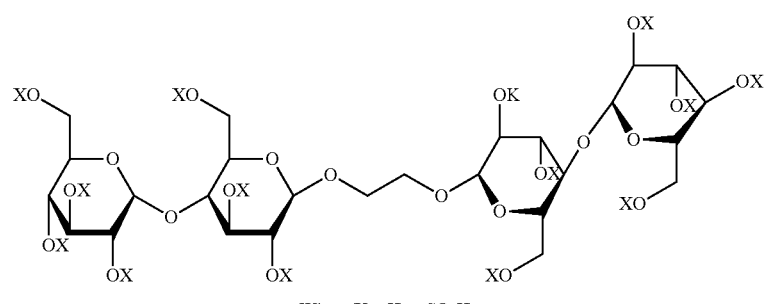
Where X = H or SO₃H
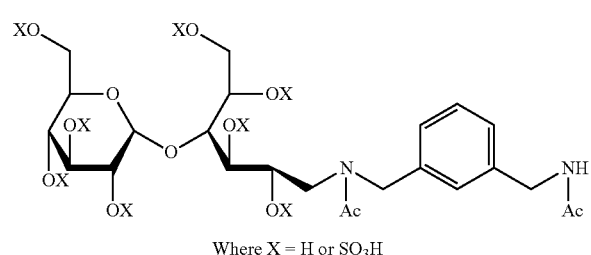
Where X = H or SO₃H
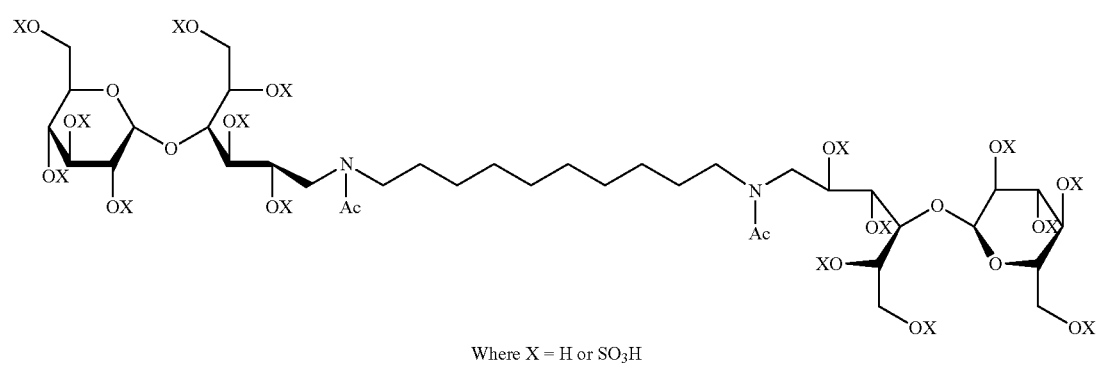
Where X = H or SO₃H

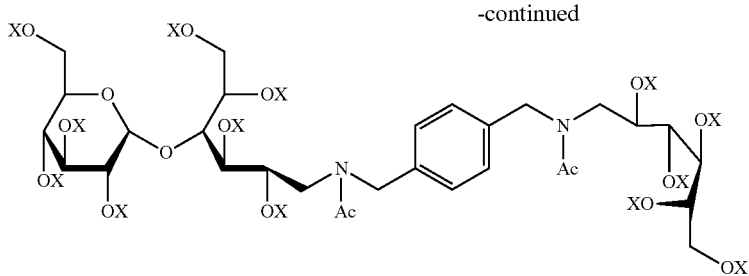

Where X = H or SO₃H

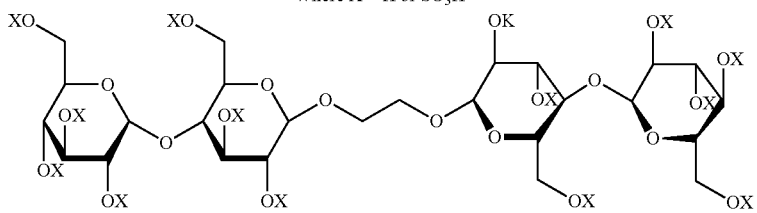

Where X = H or SO₃H

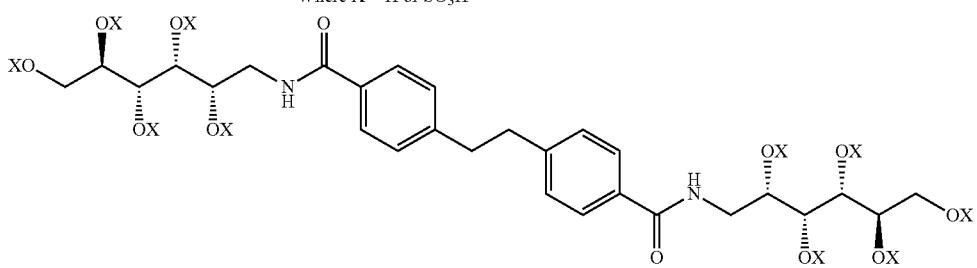

Where X = H or SO₃H

Preparation of Polyanions

Polyanions for use in the compositions and methods of the invention may be purchased or prepared by methods known to those skilled in the art.

Sulfated oligosaccharide compounds used in the methods and compositions of the invention may be prepared by sulfation of a corresponding oligosaccharide also by methods known to those skilled in the art. For example, the oligosaccharide compound may be treated with a sulfating agent such as pyridine-sulfur trioxide complex in the presence of an appropriate solvent In one aspect of the invention, the polyanion may be a mixture of compounds obtained by reaction of an oligosaccharide with pyridine-sulfur trioxide complex.

The oligosaccharide may have one or more sulfate groups present. These sulfate groups may react with various bases to form salts. The sulfated compounds are stable when in the form of a salt. The sulfated compounds in a free form may be derived from a salt thereof by utilizing a cation-exchange resin such as Dowex 50W-X8. Optionally, a salt can be subjected to conventional ion-exchange to convert it into any one of various other desirable salts.

The oligosaccharides that are sulfated may be naturally occurring products, for example raffinose, stachyose or cyclodextrins. Alternatively, the polyanions can be prepared by chemical synthesis or the oligosaccharides may be prepared by enzymatic or chemical degradation of naturally occurring polysaccharides, followed by subsequent chemical modification.

Anticoagulant Activity of Polyanions

Some polyanions may have an anticoagulant activity. The term "anticoagulant activity" refers to an activity of a substance that prevents, inhibits or prolongs blood coagulation in an in vitro or in vivo blood coagulation assay.

Blood coagulation assays are known in the art and include assays that measure the time required for the formation of a fibrin clot. For example the assay may be include prothrombin time (PT), partial thromboplastin time (PTT), activated partial thromboplastin time (APTT), fibrinogen assay, thrombin clotting time (TCT) and activated clotting time (ACT).

In some embodiments anticoagulant activity of a polyanion may impact clinical applications or effective doses of the polyanion useful in the methods described herein. However, a polyanion with anticoagulant activity is still useful in methods described herein. In a preferred embodiment the polyanion does not have substantial anticoagulant activity.

Polyanions without substantial anticoagulant activity do not substantially increase the PT, PTT, APTT, TCT or ACT compared to the normal range. For example, a polyanion that does not have substantial anticoagulant properties will not increase the PT, PTT, APTT, TCT or ACT, or the polyanion will increase the PT, PTT, APTT, TCT or ACT by 0 to about 10% of the normal range. In other embodiments the polyanion will increase the PT, PTT, APTT, TCT or ACT by about 1 to about 5% of the normal range. In a further embodiment the polyanion will increase the PT, PTT, APTT, TCT or ACT by about 2.5 to about 7.5% of the normal range. In still further embodiment the polyanion will increase the PT, PTT, APTT, TCT or ACT by about 5 to about 10% of the normal range. In a yet still further embodiment the polyanion will increase the PT, PTT, APTT, TCT or ACT by about 12.5 to about 15% of the normal range. In another embodiment the polyanion will increase the PT, PTT, APTT, TCT or ACT by about 15 to about 20% of the normal range.

Nanoparticles

U.S. Pat. No. 6,977,068 entitled "Method for detection of fibrin clots" describes methods for the use of carbon-encapsulated radionuclide nanoparticles in the detection of fibrin clots. International Patent Application No. PCT/AU2006/000554 filed 28 Apr. 2006 and published as WO 2006/116798 A1, entitled "A method of forming an injectable radioactive composition of a carbon encapsulated radioactive particulate" describes a process for the production of an injectable formulation of carbon encapsulated nanoparticles. The process described therein can be referred to as "FibrinLite process" and the nanoparticles so-produced may be referred to as "FibrinLite.

To the extent permitted, the entire contents of U.S. Pat. No. 6,977,068 and PCT/AU2006/000554 (WO 2006/116798) are incorporated herein by reference.

It will be understood that a person skilled in the art will be aware that methods of producing an aqueous dispersion of carbon encapsulated nanoparticle composites may include a step of aqueous capture of a radioactive aerosol and that this step may be achieved in a number of ways. For example, the step of aqueous capture of a radioactive aerosol used to make carbon encapsulated nanoparticle composites may include but not to be limited to collection of the aerosol in a Venturi scrubber, concentration of the aerosol on a liquid electrode, or use of a cyclone device.

In one embodiment the carbon encapsulated nanoparticle composites may be prepared using the process described in PCT/AU2006/00054, wherein the process involves capture of the radioactive aerosol in water utilising a Browitt precipitator described in U.S. Pat. No. 5,792,241 the entire contents of which are herein incorporated by reference.

As described previously carbon encapsulated nanoparticles can provide high specific radioactivity and high avidity labelling of macromolecules such as histones.

As described in PCT/AU2006/000554 a carbon encapsulated radioactive particulate (nanoparticle) may be prepared by loading a carbon crucible with technetium or other isotope, preheating the loaded crucible, flash emission of the particles, particle capture in water or other aqueous solutions.

As described in PCT/AU2006/000554 the isotope may be used to load a suitable graphite crucible either by an evaporative method if the specific activity of the isotope is sufficiently high, e.g., 100 mCi/mL, simply by placing an aliquot of the isotope in solution in the crucible and evaporating the liquid to dryness by carefully regulated resistive heating of the crucible. Alternatively the crucible may be electrolytically loaded by using the crucible as a cathode and an anode of a fine platinum wire in a fluid delivery tube. The tube delivers an isotope solution into the crucible (and facilitates its recirculation through the crucible) and the isotope can be concentrated onto the inner surface of the crucible by the combined action of the electrolysis and continuous pumping.

After loading, the crucible is subjected to a preheating step to remove any carrier in the isotope solution, for example sodium chloride is removed, preferably by evaporation into a flow of inert gas, for example, argon. The preheating step reduces the amount of free carbon subsequently ablated from the crucible, reduces the level of free isotope contaminating the nanoparticles and increases the proportion of isotope that is present in smaller particle fractions.

The pretreated crucible is flash-heated to for example 2740-2790° C. for 3 seconds by means of an electronic servo device to produce a tightly-regulated crucible heating profile featuring a rapid rise time (e.g., 0.3-0.7 seconds) followed by a flat plateau maintaining, e.g., 2765° C.±15° C. over a pre- determined heating period (e.g., 2.5-15 seconds). During this step the nanoparticles are ablated from the surface of the crucible.

The particles ablated from the crucible are precipitated in water containing a low concentration of a surfactant, e.g., 10 micromolar sodium deoxycholate and very low ionic strength conditions (e.g., less than 100 micromolar). In a preferred embodiment the nanoparticles may be precipitated in a very low concentration of a weakly acidic buffer or this may be added to the nanoparticle dispersion after collection from the precipitator, e.g., a final concentration of 300 micromolar sodium dihydrogen citrate at pH 4.1.

Accordingly, nanoparticles may be produced as a stable aqueous dispersion with a very low electrolyte concentration, less than the equivalent of 1.0 mM NaCl. Any of the methods described in PCT/AU2006/000554 or derivable therefrom for the preparation of the particles may be utilised in the preparation of the nanoparticles for use in the present invention. In one embodiment this may be achieved for example by heating the isotope loaded graphite crucible at approximately 1600-1650° C. for 15 seconds to remove carrier sodium chloride before ablation of radioisotope above 2700° C. The boiling point of sodium chloride is only 1413° C., and the Tc-99m radioisotope is not volatile at this temperature. Where alternative radioisotopes are utilized in the methods of the invention the skilled addressee will be able to determine appropriate temperature of ablation, such as by reference to PCT/AU2006/000554.

Figure 5:
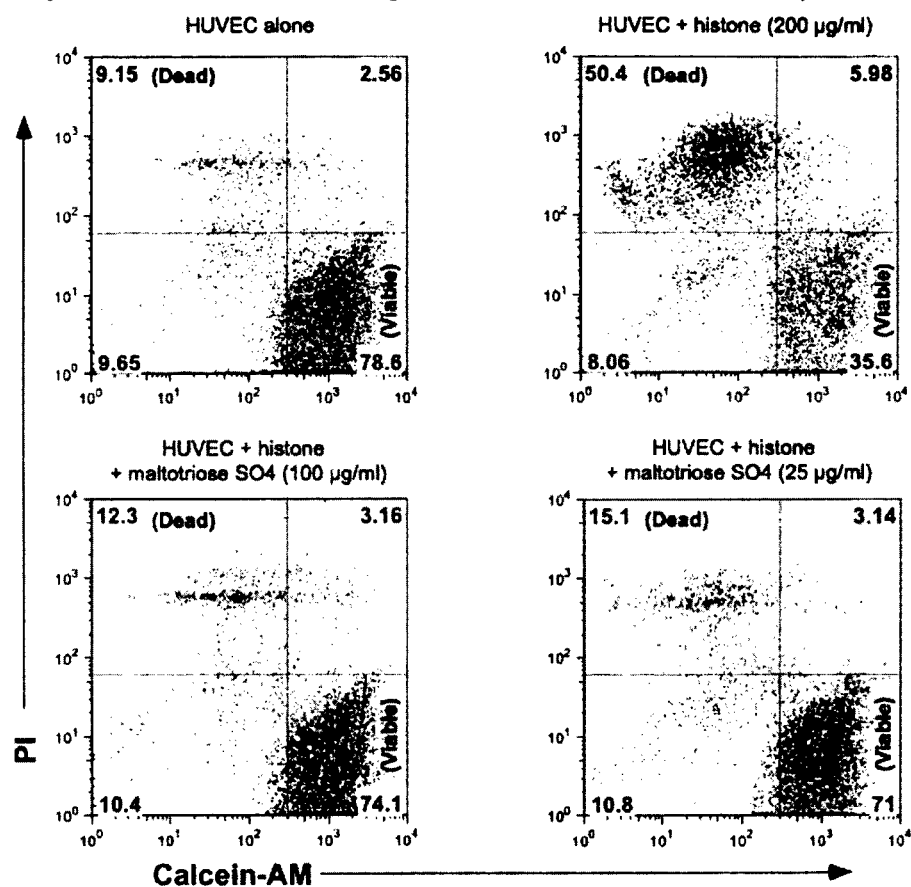
FIG. 5 depicts primary flow cytometry data showing that maltotriose sulfate at 25 μg/ml and 100 μg/ml can dramatically inhibit the in vitro cytotoxic effects of calf thymus histones (200 μg/ml) for HUVEC. Figures in each panel represent the percentage of HUVEC in each quadrant, with viable (Calcein-AM-bright, PI-dull) and dead (Calcein-AM-dull, PI-bright) cell quadrants indicated.
Figure 6:
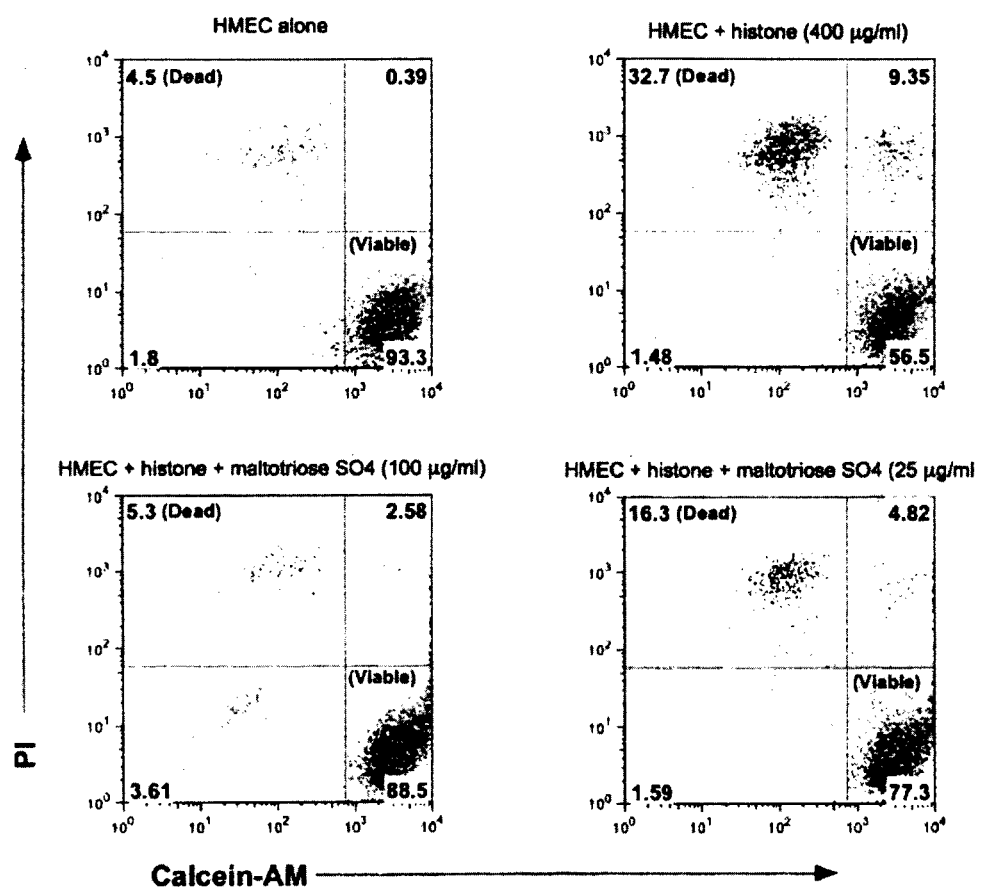
FIG. 6 depicts primary flow cytometry data showing that maltotriose sulfate at 25 μg/ml and 100 μg/ml can, respectively, totally and partially inhibit the in vitro cytotoxic effects of calf thymus histones (400 μg/ml) for HMEC. Figures in each panel represent the percentage of HMEC in each quadrant, with viable (Calcein-AM-bright, PI-dull) and dead (Calcein-AM-dull, PI-bright) cell quadrants indicated.

Aqueous dispersions of nanoparticles made according to PCT/AU2006/000554 do not flocculate, precipitate or sediment on standing for e.g. 48 hours. The dispersion of nanoparticles may contain a very low (for example, in the range of about 1 micromolar to about 20 micromolar, typically about 10 micromolar) concentration of an anionic surfactant, typically sodium deoxycholate which is compatible with and may be injected into, the blood circulation of a living subject (see FIGS. 5 and 6, herein). The nanoparticles may be stored in any appropriate manner, preferably to permit stability of the dispersion, such as by storage in a low concentration of a weakly acidic buffer, such as at a final concentration of 300 micromolar sodium dihydrogen citrate at pH 4.1. The dispersion of nanoparticles is stable, and may be size-fractionated by the use of readily available hydrophilic membrane filters, such as Millipore mixed cellulose ester (MCE) syringe filters, available with porosity of 800, 450 and 220 nm. More than 90% of the radioactivity in a typical nanoparticle preparation will pass through a 800 nm MCE filter, and the same preparation can be shown by thin-layer chromatography to contain typically less than 5% soluble isotope.

Radioactive Isotopes

The skilled addressee will appreciate that any radioisotope of a metallic element may be incorporated in the nanoparticle. As described in PCT/AU2006/000554 and PCT/AU2009/000508 a diverse range of radioisotopes may be incorporated in nanoparticles, including those that emit gamma radiation, such as Tc-99m, Ga-67; those that emit beta radiation, such as Y-90; those that emit alpha radiation, such as Bi-213; and those that emit positron radiation, such as Cu-64. Any suitable metallic radioactive isotope may be utilised, including $^{198}$Au, $^{64}$Cu, $^{213}$Bi, $^{57}$Co, $^{51}$Cr, $^{165}$Dy, $^{169}$Er, $^{59}$Fe, $^{67}$Ga, $^{68}$Ga, $^{153}$Gd, $^{166}$Ho, $^{111}$In, $^{113m}$In, $^{177}$Lu, $^{23}$Na, $^{24}$Na, $^{103}$Pd, $^{81}$Rb, $^{82}$Rb, $^{186}$Re, $^{188}$Re, $^{75}$Se, $^{153}$Sm, $^{117m}$Sn, $^{89}$Sr, $^{201}$Th, $^{90}$Y, $^{169}$Th, $^{192}$Ir.

The range of isotopes that may be used in the nanoparticles and hence in the methods of the present invention, include those that are ideally suited for diagnostic imaging applications, such as single photon computed tomography (SPECT)

using Tc-99m or Ga-67, and positron emission tomography (PET) using Cu-64 or Zr-89 or gamma scintigraphy.

As described in PCT/AU2006/000554 and PCT/AU2009/000508 an exemplary radionuclide is Tc-99m. The nanoparticles can each carry tens of thousands or more of isotope atoms in their core, so that very high levels of specific activity can readily be obtained that are well above those obtainable with traditional labelling methods. For, and using Tc-99m as the model encapsulated radioisotope, a Tc-99m loading in the range of from about 1 to about 100 mCi, about 5 to about 100 mCi, about 7.5 to about 95 mCi, about 10 to about 90 mCi, about 15 to about 85 mCi, about 20 to about 80 mCi, about 25 to about 75 mCi, about 30 to about 70 mCi, about 35 to about 65 mCi, about 40 to about 60 mCi, about 45 to about 55 mCi, or about 50 to about 55 mCi may be prepared. A typical preparation of particles can readily be made so as to contain between about 1 and about 30 mCi in 2 mL of aqueous suspension, as desired. From vapour phase characterization of the particles using scanning mobility particle sizing (SMPS), it can be shown that the suspension can contain approximately 50 μg of nanoparticle material, so that the specific activity can be made as high as 600 mCi/mg, or over 22 GBq/mg. The specific activity of the preparation may be adjusted as desired by varying the activity of isotope used to load the crucible in the aerosol generator.

Labelling Histones with Nanoparticles

In preferred embodiments the labelling of histones is substantially irreversible under conditions typically encountered by the labelled histone in vivo. Typically, the high avidity labelling of the histone is such that there is less than about 10% dissociation under in vivo conditions. International Patent Application No. PCT/AU2009/000508 filed 23 April 2009 and published as WO 2009/129577 A1, entitled "Methods for radiolabelling macromolecules" describes a process for the labelling of biological macromolecules such as polypeptides. To the extent permitted, the entire contents of PCT/AU2009/000508 (WO 2009/129577) are incorporated herein by reference.

PCT/AU2009/000508 describes a method by which radiolabelled macromolecules may be prepared using nanoparticles, the present inventors take advantage of the carbon encapsulation process (see PCT/AU2006/000554) which wraps a metallic isotope in a carbon cage, so that it becomes physically isolated from contact with its external environment, an especially valuable property for the particles and hence the macromolecule, particularly when they are to be used in vivo. The potential for leaching and bio-uptake of the radioactive metal ions in vivo of the radiolabelled macromolecule is virtually non-existent because only the carbon exterior of the nanoparticle composite is exposed to the biological environment in vivo.

PCT/AU2009/000508 describes methods by which nanoparticles can be coated with polycations such as a histone, so that the resulting particles have a core of high specific activity of detectable radiolabel as well as tightly bound histone.

The radiolabelled histone may be used to localise a readily detectable isotope at a pre-determined site in vivo, based on the specific biological interaction that the histone has with an organ, such as the lung. For example, as demonstrated herein, Tc99m nanoparticles in complex with calf thymus histones are selective for lung tissue and when administered to a subject will preferentially target the lung, as visualized by gamma scintigraphy. In this manner the histone coated nanoparticles can be used as a screening agent for testing the ability of candidate compounds to inhibit the accumulation of histones in the lung.

Conditions for Radiolabelling Histones Using Nanoparticles

The nanoparticles so-produced or obtained may be used in the methods described in PCT/AU2009/000508 for radiolabelling histones.

Hydrophobic interfaces, such as an air-water interface, hydrocarbon-water interfaces and by inference a graphite-water interface as in aqueous nanoparticle suspensions, generally attract a slight predominance of hydroxyl ions in pure water. The result is that these interfaces behave as slightly negatively charged, although the surface potentials are usually very low (tens of millivolts). The nanoparticles may also bear increased negative charge on their surface due to adsorption of the anionic surfactant, typically deoxycholate, that is used in their preparation. If the particles and a macromolecule are similarly negatively charged in the same aqueous medium they may weakly repel each other at the tens of nanometers scale when their diffuse double layers of charges overlap. However, the selection of a pH of the aqueous medium in which the nett charge on the histone is substantially zero, such as at the pt of the histone, very is rapidly screens this potential such that it offers little energetic barrier to the adsorption and cohesion of particles to a macromolecule in these systems. Such screening, at Debye lengths <10 nm, will produce a situation in which attractive dispersion, ion correlation or hydrophobic forces will usually dominate the total interaction energy of these surfaces. The result is that particles once engaged with the histone will tenaciously adhere to that macromolecule in an essentially irreversible manner. The conditions thereby promote avid binding of the histone and nanoparticle composite. In preferred embodiments the medium in which the contacting occurs may comprise a pH and an electrolyte concentration which promotes the influence of short range attractive forces between the nanoparticles and the histone over the long-range electrostatic repulsive forces by diminishing the latter in extent and magnitude. As a result of successful contacting the macromolecule may be described as being associated with or complexed with the nanoparticle composite. The resultant entity may also be referred to as a complex. It is noted that the terms "complex" and "complexed with" in the present context are not intended to imply any particular structural arrangement of the histone and nanoparticle composite other than what occurs as a result of successful contacting in which they become tightly bound.

The nanoparticles may be used to label a histone by contacting the nanoparticles and the macromolecule under conditions of suitable pH and preferably also suitable electrolyte concentration. Suitable solution conditions can be selected that facilitate the screening process described above and thus enable short-range attractive forces to dominate over repulsive electrostatic forces, such that the nanoparticles become virtually irreversibly bound to a macromolecule. In view of the disclosure herein it will be appreciated that appropriate and, if desired, optimal, binding conditions, such as pH and electrolyte concentration, can be determined empirically for a desired contacting between nanoparticles and a histone.

The contacting may occur in any suitable medium, although an aqueous medium will usually be preferred. Prior to the contacting, the nanoparticles may be prepared in or stored in a suitable storage medium, generally selected to permit stability of the dispersion. Thus the dispersion of nanoparticles may contain a very low (for example, about 10 micromolar) concentration of an anionic surfactant, such as sodium deoxycholate. Prior to the contacting step of the method of the invention, the nanoparticles may be pre-treated to adjust the conditions of the dispersion to favor binding of the nanoparticles and histone. For example, conditions such as buffer type, pH, electrolyte concentration and type, presence or absence of surfactant and concentration of any component, including of the nanoparticles, may be adjusted. Adjustment of the pH and ionic strength of the medium may occur in the presence or absence of the histone. Typically adjustment of the pH and ionic strength of the medium, when in the presence of the nanoparticles, will occur in the presence also of the macromolecule so as to promote the binding between nanoparticles and the macromolecule, rather than binding only between nanoparticles that will cause aggregation and clumping.

Binding of nanoparticles to a histone may be achieved through the use of a pH near the pI of the macromolecule and a suitable concentration of the simple electrolyte NaCl, which is effective in inducing avid binding of the nanoparticles to the macromolecule at concentrations of greater than about 1 mM NaCl. As will be appreciated, appropriate conditions for inducing avid binding of nanoparticles to a histone may be achieved using any one or more of a large variety of electrolytes. A simple electrolyte concentration of greater than about 1 millimolar may be used to induce avid binding of nanoparticles to a histone and thus, where the nanoparticles have a radioactive particulate core, to provide for the preparation of a radiolabelled histone. Generally, the simple electrolyte concentration of the solution or medium for the contacting is expected to be in the range of about 1 millimolar to about 200 millimolar; typically, about 10 millimolar to about 175 millimolar; about 20 millimolar to about 150 millimolar; about 50 millimolar to about 150 millimolar. More typically the electrolyte concentration of the solution is expected to be in the range of about 1 millimolar to about 200 millimolar; typically from about 10 millimolar to about 175 millimolar; from about 20 millimolar to about 150 millimolar; from about 40 millimolar to about 150 millimolar; from about 50 millimolar to about 150 millimolar; from about 75 millimolar to about 150 millimolar; from about 90 millimolar to about 150 millimolar; from about 100 millimolar to about 150 millimolar; about 150 millimolar. A person of skill in the art will understand that the ionic strength of an electrolyte solution or medium for the contacting step of the present invention may be achieved by, for example, using NaCl wherein a suitable ionic strength may be achieved with an NaCl concentration of about 150 mM or, for example, a $MgSO_4$ concentration of less than about 75 mM. A person of skill in the art will also understand that a suitable ionic strength of an electrolyte solution may be achieved by use of a number of different ionic species, for example a mixture of NaCl and $MgSO_4$. Furthermore a person of skill in the art will understand the ionic strength may be achieved by use of at least one ionic species and at least one non-ionic species such as an osmolyte or high molecular weight polymer such as polyethylene glycol. For example, where the effective concentration of water is reduced, the concentration of electrolyte may need to be increased, for example at about 250 mM.

Any suitable ionic species may be used. For example, the ionic species may be selected from the group comprising salts of Na, Ni, Al, Ru, Pt, Os, Ir, Fe, Se, Sn, K, Te, Mn, Mo, V, Mg, Zn, Ca, Cu, Co. In preferred embodiments the ionic species will typically be limited to those that are non-toxic at the effective concentrations, e.g. Na, K, Ca.

The buffer used in the contacting step may be of any suitable pH selected to be suitable for promoting short-range attractive forces between the nanoparticles and the histone by suppressing repulsive electrostatic forces. Preferably the buffer will be in the range from about pH 3 to about pH 10 or greater, from about pH 3 to about pH 8, from about pH 3.5 to about pH 8.5, from about pH 4 to about pH 8, from about pH 4.5 to about pH 7.5, from about pH 5 to about pH 7. More preferably the pH of the contacting step, such as the pH of the aqueous medium, will be near to the pI of the macromolecule to be utilised in the contacting, such as a polypeptide. More preferably still, the pH of the contacting step will be substantially at the pI of the macromolecule to be utilised in the contacting. As described herein the desired and optimal pH can be determined by the skilled addressee taking into account other reaction conditions, such as the electrolyte(s) type and concentration and the macromolecule(s).

The contacting may comprise modification of the conditions during the course of the contacting, such as an increase or decrease in the temperature of incubation during the contacting, or an increase or decrease of agitation of the medium or mixing during the contacting.

The radiolabelled histone may be subjected to one or more purification steps subsequent to the contacting. This may comprise separating radiolabelled macromolecule from unlabelled macromolecule and/or from free nanoparticle composite. In a typical reaction the contacting may result in satisfactory binding of nanoparticles to a histone to provide radiolabelled histone, whilst retaining in the aqueous media of the contacting step unreacted components, typically a proportion of nanoparticles composite which have not become attached to the histone. Removal of unreacted components may be desirable, for to example in circumstances where free nanoparticles composite would be detrimental, such as blood transport to non-target organs. Removal of unbound macromolecule is desirable in the case where it will otherwise compete with the labeled macromolecule for specific binding sites, such as cell receptors or antigen sites, and thereby diminish the imaging capability or screening sensitivity. The removal of unreacted components may be partial, substantially complete or complete. In this context "partial" removal will be understood to include removal of any amount of one or more unreacted or undesired components, more typically removal of up to about 80%, 90% or 95% of one or more unreacted or undesired components and "complete" removal will be understood to be removal of greater than about 95% of one or more unreacted or undesired components. Typically removal of at least 95% of unreacted or undesired components is preferred, more preferably removal of greater than about 96%, 97%, 98%, or 99% of unreacted or undesired components.

Hence it will be understood that reference to "purification" in this context is intended to mean any degree of purification, whereby the radiolabelled macromolecule (or macromolecule 'labelled' with an inactive progenitor of a radioisotope) after a "purification" step contains less impurities, such as unreacted or undesired components of the contacting, compared to before the purification step.

Any method capable of separating radiolabelled histone from unreacted or undesired components, such as unbound radioactive nanoparticles or histone, may be used in a purification step. For example, the method may comprise washing one or more undesired components away from the radiolabelled histone, or may comprise extracting the radiolabelled histone away from the one or more undesired components, or may comprise centrifugation at high speed, or may comprise a combination of such steps.

Methods for Coating of Nanoparticle Composites with Histones.

The nanoparticle composites of carbon encapsulated radionuclides may be prepared according to PCT/AU2006/000554. A neutral or slightly acid pH, stable aqueous dispersion of nanoparticles comprising carbon-encapsulated radionuclide (e.g. Tc-99m) can be produced. The dispersion of nanoparticles may also contain a very low (e.g., 10 micromolar) concentration of an anionic surfactant, sodium deoxycholate, which is compatible with and may be injected into, the blood circulation of a living subject (see FIGS. 5 and 6 herein). These particles can each carry tens of thousands or more of isotope atoms as the labelling source, so that very high levels of specific activity can readily be obtained that are well above those obtainable with traditional labelling methods. For nanoparticle composites with Tc-99m as the model encapsulated radioisotope, a typical preparation of nanoparticles can readily be made so as to contain between 1 and 30 mCi in 2 mL of aqueous suspension, as desired. From vapour phase characterization of the particles using scanning mobility particle sizing (SMPS) techniques, it can be shown that this suspension contains approximately 50 μg of nanoparticle material, so that the specific activity can be made as high as 600 mCi/mg, or over 22 GBq/mg.

The carbon encapsulation process wraps the metallic isotope in a carbon cage, so that it becomes physically isolated from contact with its external environment, an especially valuable property for the particles when they are to be used in vivo. The potential for leaching and bio-uptake of the radioactive metal ions in vivo is virtually non-existent. Only the carbon exterior of the nanoparticle composite is exposed to the biological environment in vivo. Because the carbon is in a graphitic form, it has natural adsorbent properties, and this can be used as the basis for physico-adsorption to selected polypeptides. It is first required however to determine appropriate conditions that will favour attachment of polypeptides, and the following studies and examples illustrate how these conditions can be determined.

The nanoparticle composites are capable of high avidity binding via hydrophobic or dispersion interactions, involving their graphitic surface. In order for the graphitic surface to form hydrophobic interactions with macromolecules, such as polypeptides, the polypeptide must be able to approach the graphite surface at very close range, thus in turn necessitating that repulsive electrostatic forces are suppressed. The inventors show that this condition can be met when the polypeptide is presented to the nanoparticle preparations with minimum net surface charge, either by adjusting the pH to near the isoelectric point of the polypeptide, or by shielding the charge of the polypeptide with an appropriate concentration of electrolyte counterions. Empirical binding experiments may be used to establish appropriate binding conditions.

Methods of Screening

The present invention provides methods of screening for a compound that modulates the activity of one or more histones. In general these methods comprise contacting the histone with a candidate compound under conditions suitable to enable interaction of the candidate compound and the histone and assaying for activity or loss of activity of the histone.

The histone may be selected from H1, H2A, H$_2$B, H3, H4 or H5. The histone may also comprise a mixture of different histones eg calf thymus histones. In some embodiments variants, fragments and analogues of a histone may be used.

In one embodiment a method for screening histone binding compounds is provided. The method utilises administration of one or more radiolabelled histones to a test subject followed by administration of one or more candidate compounds to the test subject. The radiolabelled histone is then imaged and the location of the radiolabelled histone enables assessment of the ability of the candidate compounds to inhibit histone accumulation in an organ such as the lung.

In other embodiments the candidate compound may be administered to the test subject before or at the same time as the radiolabelled histone. Alternatively the candidate compound may be mixed with the radiolabelled histone before administration of the mixture to test subject.

External imaging by methods known in the art such as single photon computed tomography (SPECT), positron emission tomography (PET) or gamma scintigraphy may be used. In other embodiments, histones may be labelled with fluorescent dyes such as FITC (fluorescein isothiocyanate) or quantum dots. In another embodiment the histone may be labelled with a bioluminescent moiety. The location and concentration of the labelled histone may thus be determined in vivo.

Imaging by any modality known in the art may then reveal the presence or overabundance of the labelled histone at a tissue or organ site that may be due to a failure of a candidate compound to inhibit histone accumulation. Similarly a decrease in the abundance of the labelled histone at a tissue or organ, compared to a control labelled histone in the absence of the test compound indicates that a candidate compound inhibits the histone and prevents accumulation at the tissue or organ.

It should be noted that when intravenously injected, the unlabelled nanoparticle composites are almost completely removed from the circulation within 20 minutes by the reticuloendothelial system, i.e. phagocytic cells such as the Kupffer cells of the liver. Thus the presence or overabundance of the labelled histone in the liver, spleen and bone marrow may indicate the rapid clearance of circulating nanoparticles by the reticuloendothelial system that may be due to a candidate compound inhibiting histone binding to the lung for example.

Histones, variants, fragments and analogues thereof are useful for the screening and identification of compounds and agents that interact with these molecules. In particular, desirable compounds are those that modulate the activity of these molecules. Such compounds may exert a modulatory effect by inhibiting the function of histone, variants, fragments and analogues thereof. Further, histone variants, fragments and analogues thereof are useful for the screening and identification of compounds and agents that promote degradation of histones. Suitable compounds may exert their effect by virtue of either a direct (for example binding) or indirect interaction. Alternatively or additionally suitable compounds may exert their effect by modulating the interaction of histone, variants, fragments and analogues thereof with other proteins or peptides.

Compounds which bind, or otherwise interact with histones and specifically compounds which modulate their activity or promote their degradation, may be identified by a variety of suitable methods. Non limiting methods include, co-immunoprecipitation, immunological based detection methods such as western blotting, affinity chromatography, gel filtration, gel mobility assays, mass spectroscopy, tandem affinity purification, phage display, label transfer, protein microarrays.

Further, the ability of a candidate compounds that bind, or otherwise interact with histones and which modulate the activity or promote degradation of histones may be assessed by the effect of those candidate compounds on the function of histones. The function may be measured according to any method known in the art.

Affinity Chromatography

Affinity chromatography may be used to determine whether a candidate agent or plurality of candidate agents interacts or binds with a histone or a variant or fragment thereof. For example, histone, variants, fragments or analogues thereof, may be immobilised on a support (such as Sepharose) and candidate compounds either alone or in mixtures passed over the column. Compounds binding to the immobilised histone polypeptide or a variant or fragment thereof may then be eluted from the column and identified, for example by mass spectrometry.

In this way, proteins or other compounds that do not directly interact with histones, variants fragments or analogues thereof may be identified. For example, a compound that interacts directly with a histone may in turn be associated with an agent that may modulate histone activity without direct interaction with the histone. The interaction of the complex of the compound and associate agent with the immobilised histone polypeptide or a variant or fragment thereof will facilitate identification of compounds that may modulate histone activity without direct interaction with the histone.

Potential modulators of histone activity may be generated for screening by the above methods by a number of techniques known to those skilled in the art. For example, methods such as X-ray crystallography and nuclear magnetic resonance spectroscopy may be used to model the structure of histones, variants fragments or analogues thereof, thus facilitating the design of potential modulating agents using computer-based modeling. Various forms of combinatorial chemistry may also be used to generate putative modulators.

Histones, variants, fragments or analogues thereof can be used in high-throughput screens to assay candidate compounds for the ability to bind to, or otherwise interact therewith. These candidate compounds can be further screened against functional histone, variants fragments or analogues thereof to determine the effect of the compound on enzyme activity.

Immunological Methods

Immunological methods may be used to determine whether a candidate agent or plurality of candidate agents interacts or binds with a histone or a variant or fragment thereof. In one embodiment a histone or a variant or fragment thereof may be contacted with at least one candidate compound before using immunoprecipation to determine whether a candidate agent or plurality of candidate agents interacts or binds with a histone or a variant or fragment thereof. Using this technique, at least one candidate compound may be contacted with a histone or a variant or fragment, typically by mixing solutions of each. That mixture (sample) can then be incubated with an antibody specific for either the candidate compound or the histone which can immunoprecipitated from the solution, for example by capture with an antibody-binding protein attached to a solid support. Immunoprecipitation of a protein by this method facilitates the co-immuno-precipitation of an agent associated with that protein. The identification an associated agent can be established using a number of methods known in the art, including but not limited to SDS-PAGE, western blotting, and mass spectrometry.

Antibodies specific for a candidate compound or a histone may be immobilised on a support. To detect a candidate compound associate with the histone typically involves contacting the immobilised antibody with a sample putatively containing a candidate compound associated with a histone under conditions suitable for binding between the immobilised antibody and the histone or candidate compound, and rinsing the support with a suitable reagent to remove unbound sample. Subsequently the bound sample putatively containing a candidate compound associated with a histone can be eluted for example by rinsing with a denaturant and the identity of the components of the bound sample can be established using a number of methods known in the art, including but not limited to SDS-PAGE, western blotting, and mass spectrometry.

The antibody may be immobilised on the support by direct binding or be bound indirectly to the support via one or more additional compounds. Non-limiting examples of suitable supports include assay plates (e.g. microtiter plates) or test tubes manufactured from polyethylene, polypropylene, or polystyrene, polyvinyl chloride, membranes (e.g. nitrocellulose membranes), beads/discs (including magnetic beads and discs) and particulate materials such as filter paper, nitrocellulose membrane, Sepharose, agarose, cross-linked dextran, and other polysaccharides.

In certain embodiments, the detection of a candidate agent or plurality of candidate agents that interacts or binds with a histone or a variant or fragment thereof is performed as an enzyme-linked immunosorbent assay (ELISA). In general, the assay involves the coating of a suitable capture reagent onto a solid support, such as the wells of a microtitre plate or a column, manufactured from a material such as polyethylene, polypropylene, polystyrene and the like. In one embodiment an anti-histone antibody is used as a capture reagent. In another embodiment, the capture reagent is prepared by coating at least one candidate compound onto the solid support. In a further embodiment the capture reagent may be heparin, heparan sulfate, bovine serum albumin conjugated heparan sulfate, heparan sulfate proteoglycan (e.g. perlecan), mammalian cells or the like. In another embodiment the histone may be used as the capture reagent.

The capture reagent may be linked to the surface of the support, for example, by a non-covalent or covalent interaction or a physical linkage. If a covalent linkage is used, the cross-linking agent may be utilised to attach the capture reagent to the support (e.g. glutaraldehyde, N-hydroxy-succinimide esters, bifunctional maleimides).

The support may be treated with a blocking agent (e.g. non-fat milk, bovine serum albumin, casein, egg albumin) to prevent unwanted binding of material to excess sites on the surface of the support.

The sample may be administered to the surface of the support following coating and blocking. In general, the sample is diluted to an appropriate level using a suitable buffer. The degree of sample dilution and selection of an appropriate buffer will depend on factors such as the sample under analysis and the type of support and capture reagent utilised in the assay. These can be determined without inventive effort by those of ordinary skill in the art.

Once applied to the support coated with capture reagent, the sample is generally incubated under conditions suitable to maximize sensitivity of the assay and to minimize dissociation. The incubation may be performed at a generally constant temperature, ranging from about 0° C. to about 40° C., and preferably ranging from about 20° C. to about 30° C. The pH of the incubation mixture may be in the range of about 4 to about 10, is preferably in the range of about 6 to about 9, and more preferably in the range of about 7 to about 8. In one embodiment, the incubation mixture is at pH 7.4. Various buffers may be employed to achieve and maintain the target pH during the incubation, non-limiting examples of which include Tris-phosphate, Tris-HCl, borate, phosphate, acetate and carbonate. The incubation time is generally associated with the temperature, and may be less than about 12 hours to avoid non-specific binding. Preferably, the incubation time is from about 0.5 hours to about 3 hours, and more preferably from about 0.5 hours to about 1.5 hours at room temperature.

Following incubation, the biological sample may be removed from the immobilised capture reagent to remove unbound sample, for example, by washing/rinsing the support. The pH of a suitable washing buffer may be in the range of about 6 to about 9 and preferably in the range of about 7 to about 8. The washing/rinsing may be done three or more times. The washing/rinsing may be performed using wash buffer generally at a temperatures from about 0° C. to about 40° C., and preferably from about 4° C. to about 30° C.

In a subsequent step, immobilised components of the sample bound to the capture reagent may be contacted with a detection reagent. The choice of detectable reagent can depend on factors including the capture reagent utilised and the type of sample under analysis. Preferably, immobilised molecules of the sample bound to the capture reagent are contacted with a detection reagent at a temperature of about 20° C. to about 40° C., and preferably at a temperature of about 20° C. to about 25° C. In one embodiment, immobilised molecules of the sample bound to the capture reagent are contacted with a detection reagent at room temperature (RT) for about one hour. The detection reagent may be an antibody. In applications where the detectable reagent is an antibody, a molar excess of the antibody with respect to the maximum concentration of the molecules of the sample immobilised on the support is preferable. The antibody may be directly or indirectly detectable. The antibody may have a colorimetric label or a fluorometric label. An additional antibody may be used that binds to the detection reagent. The additional antibody may have a colorimetric label or a fluorometric label.

Determination of the presence and levels of a sample bound to the capture reagent can be achieved using methods known in the art, and will depend upon the detection reagent utilised. For example, detection may include colorimetry, chemiluminescence, or fluorometry. Detection and quantitative measurements may be conducted based on the signal derived from the detection reagent(s) compared to background signal derived from control samples.

Treatment of Sepsis

Treatment of sepsis typically involves treatment of the underlying cause of the condition for example by antibiotic therapy. While alternative treatments have been developed e.g activated protein C (APC) these have had little clinical impact due to the anticoagulant properties of the therapeutic or the slow mode of action relative to the rapid progression of sepsis.

Histone toxicity has recently been identified as a mediator of endothelial cell dysfunction, organ failure and death in sepsis. The inventors have found that oligosaccharide polyanions, that may have insignificant anticoagulant properties, can complex with histones in the circulation of a living animal and prevent histone accumulation in organs. This provides the basis for a treatment of sepsis which typically involves the administration of at least one polyanion to a patient in need of such treatment.

Compositions, Dosages and Routes of Administration

Polyanion(s) for use in the present invention may be administered as compositions either therapeutically or preventively. In a therapeutic application, compositions are administered to a subject already suffering from a disease (e.g. sepsis), in an amount sufficient to resolve or partially arrest the disease and/or its complications or to improve the survival of a patient.

In general, suitable compositions may be prepared according to methods which are known to those of ordinary skill in the art and accordingly may include a pharmaceutically acceptable carrier, diluent and/or adjuvant.

Methods for preparing administrable compositions are apparent to those skilled in the art, and are described in more detail in, for example, *Remington's Pharmaceutical Science*, 15th ed., Mack Publishing Company, Easton, Pa., hereby incorporated by reference in its entirety.

The polyanion may be present as a pharmaceutically acceptable salt. By "pharmaceutically acceptable salt", it is meant those salts which, within the scope of to sound medical judgement, are suitable for use in contact with tissues of humans and lower animals without the undue toxicity, irritation, allergic response and the like, and are commensurate with a reasonable benefit/risk ratio. Pharmaceutically acceptable salts are well known in the art.

The therapeutically effective amount of a polyanion disclosed herein for any is particular subject will depend upon a variety of factors including: the severity of the sepsis; activity of the compositions employed; the age, body weight, general health, sex and diet of the patient; the time of administration; the route of administration; the rate of sequestration of the compositions; the duration of the treatment; drugs used in combination or coincidental with the treatment, together with other related factors well known in medicine.

One skilled in the art would be able, by routine experimentation, to determine an effective, non-toxic amount of the components of the formulations which would be required to achieve the desired outcome of the methods of the invention.

Generally, an effective dosage of polyanion is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage of polyanion may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Further, it will be apparent to one of ordinary skill in the art that the optimal quantity and spacing of individual dosages will be determined by the nature and extent of the sepsis being treated, the form, route and site of administration, and the nature of the particular individual being treated. Also, such optimum conditions can be determined by conventional techniques. In some therapeutic applications, the treatment would be for the duration of the sepsis.

It will also be apparent to one of ordinary skill in the art that the optimal course of treatment, such as, the number of doses of the polyanion given per hour or day for a defined number of hours or days, can be ascertained by those skilled in the art using conventional course of treatment determination tests.

In general, suitable compositions may be prepared according to methods which are known to those of ordinary skill in the art and accordingly may include a pharmaceutically acceptable carrier, diluent and/or adjuvant.

Convenient modes of administration include injection (subcutaneous, intravenous, intraarterial etc.), oral administration, intranasal or inhalation. Depending on the route of administration, the formulation and/or polyanion may be coated with a material to protect the polyanion from the action of enzymes, acids and other natural conditions which may inactivate the therapeutic activity of the compound. The polyanion may also be administered parenterally or intraperitoneally.

Dispersions of polyanion(s) may also be prepared in glycerol, liquid polyethylene glycols, and mixtures thereof and in oils. Under ordinary conditions of storage and use, pharmaceutical preparations may contain a preservative to prevent the growth of microorganisms.

Pharmaceutical compositions suitable for injection include sterile aqueous solutions (where water soluble) or dispersions and sterile powders for the extemporaneous preparation of sterile injectable solutions or dispersions. Ideally, the composition is stable under the conditions of manufacture and storage and may include a preservative to stabilise the composition against the contaminating action of microorganisms such as bacteria and fungi.

In one embodiment of the invention, the polyanion(s) may be administered orally, for example, with an inert diluent or an assimilable edible carrier. The polyanion(s) and other ingredients may also be enclosed in a hard or soft shell gelatin capsule, compressed into tablets, or incorporated directly into an individual's diet. For oral therapeutic administration, the polyanion(s) may be incorporated with excipients and used in the form of ingestible tablets, buccal tablets, troches, capsules, elixirs, suspensions, syrups, wafers, and the like. Suitably, such compositions and preparations may contain at least 1% by weight of active polyanion. The percentage of the polyanion in pharmaceutical compositions and preparations may, of course, be varied and, for example, may conveniently range from about 2% to about 90%, about 5% to about 80%, about 10% to about 75%, about 15% to about 65%; about 20% to about 60%, about 25% to about 50%, about 30% to about 45%, or about 35% to about 45%, of the weight of the dosage unit. The amount of polyanion in therapeutically useful compositions is such that a suitable dosage will be obtained.

In another embodiment of the invention, the polyanion may be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference.

The language "pharmaceutically acceptable carrier" is intended to include solvents, dispersion media, coatings, antibacterial and anti-fungal agents, isotonic and absorption delaying agents, and the like. Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The use of such media and agents for pharmaceutically active substances is well known in the art. Except insofar as any conventional media or agent is incompatible with the polyanion, use thereof in the therapeutic compositions and methods of treatment and prophylaxis is contemplated. Supplementary active compounds may also be incorporated into the compositions according to the present invention. It is especially advantageous to formulate parenteral compositions in dosage unit form for ease of administration and uniformity of dosage. "Dosage unit form" as used herein refers to physically discrete is units suited as unitary dosages for the individual to be treated; each unit containing a predetermined quantity of polyanion(s) is calculated to produce the desired therapeutic effect in association with the required pharmaceutical carrier. The polyanion(s) may be formulated for convenient and effective administration in effective amounts with a suitable pharmaceutically acceptable carrier in an acceptable dosage unit. In the case of compositions containing supplementary active ingredients, the dosages are determined by reference to the usual dose and manner of administration of the said ingredients.

In one embodiment, the carrier may be an orally administrable carrier.

Another form of a pharmaceutical composition is a dosage form formulated as enterically coated granules, tablets or capsules suitable for oral administration.

Also included in the scope of this invention are delayed release formulations.

The polyanion may also be administered in the form of a "prodrug". A prodrug is an inactive form of a compound which is transformed in vivo to the active form. Suitable prodrugs include esters, phosphonate esters etc, of the active form of the polyanion.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colorings agents. When used in capsule form the capsules may be coated with compounds such as glyceryl monostearate or glyceryl distearate which delay disintegration.

In one embodiment, the compound may be administered by injection. In the case of injectable solutions, the carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by including various anti-bacterial and/or anti-fungal agents. Suitable agents are well known to those skilled in the art and include, for example, parabens, chlorobutanol, phenol, benzyl alcohol, ascorbic acid, thiomerosal, and the like. In many cases, it may be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminium monostearate and gelatin.

Sterile injectable solutions can be prepared by incorporating the polyanion in the required amount in an appropriate solvent with one or a combination of ingredients enumerated above, as required, followed by filtered sterilisation. Generally, dispersions are prepared by incorporating the analogue into a sterile vehicle which contains a basic dispersion medium and the required other ingredients from those enumerated above.

Tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin or a flavouring agent such as peppermint, oil of wintergreen, or cherry flavouring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the analogue, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the analogue can be incorporated into sustained-release preparations and formulations.

The pharmaceutical compositions may further include a suitable buffer to minimise acid hydrolysis. Suitable buffer agent agents are well known to those skilled in the art and include, but are not limited to, phosphates, citrates, carbonates and mixtures thereof.

Single or multiple administrations of the pharmaceutical compositions according to the invention may be carried out. One skilled in the art would be able, by routine experimentation, to determine effective, non-toxic dosage levels of the polyanion and/or and an administration pattern which would be suitable for treating sepsis.

Combination Regimens

Therapeutic advantages may be realised through combination regimens. Those skilled in the art will appreciate that the polyanions described herein may be administered as part of a combination therapy approach to the treatment of sepsis. In combination therapy the respective agents may be administered simultaneously, or sequentially in any order. When administered sequentially, it may be preferred that the components be administered by the same route.

Alternatively, the components may be formulated together in a single dosage unit as a combination product. Suitable agents which may be used in combination with the compositions of the present invention will be known to those of ordinary skill in the art.

Methods of treatment according to the present invention may be applied in conjunction with conventional therapy. Conventional therapy may also comprise administration of anti-inflammatory agents, antibiotic agents, antiviral agents, antifungal agents or other forms of medical intervention for example the use of APC.

Examples of anti-inflammatory agents include steroids, corticosteroids, COX-2 inhibitors, non-steroidal anti-inflammatory agents (NSAIDs), aspirin or any combination thereof.

Examples of antibiotic agents include aminoglycosides, ansamycins, carbacephems, carbapenems, cephalosporins, glycopeptides, lincosamides, macrolides, monobactams, penicillins, polypeptides, quinolones sulfonamides and tetracyclines.

Examples of antiviral agents include non-nucleoside reverse transcriptase inhibitors, nucleoside reverse transcriptase inhibitors (e.g. nucleoside analogues), protease inhibitors and nucleotide analogue reverse transcriptase inhibitors.

Examples of antifungal agents include imidazoles, triazoles, thiazoles, allylamines, and echinocandins.

Polyanions disclosed herein may be administered either therapeutically or preventively. In a therapeutic application, compounds and compositions are administered to a patient already suffering from sepsis, in an amount sufficient to cure or at least partially arrest the sepsis and its symptoms and/or complications. The compound or composition should provide a quantity of the active compound sufficient to effectively treat the patient.

Polyanions disclosed herein may be administered to patients before sepsis is clinically apparent, for example in patients who are risk of developing sepsis.

Carriers, Diluents, Excipients and Adjuvants

Carriers, diluents, excipients and adjuvants must be "acceptable" in terms of being compatible with the other ingredients of the composition, and not deleterious to the recipient thereof. Such carriers, diluents, excipient and adjuvants may be used for enhancing the integrity and half-life of the compositions of the present invention. These may also be used to enhance or protect the biological activities of the compositions of the present invention.

Examples of pharmaceutically acceptable carriers or diluents are demineralised or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrolidone; agar; gum tragacanth or gum acacia, and petroleum jelly. Typically, the carrier or carriers will form from 10% to 99.9% by weight of the compositions.

The carriers may also include fusion proteins or chemical compounds that are covalently bonded to the compounds of the present invention. Such biological and chemical carriers may be used to enhance the delivery of the compounds to the targets or enhance therapeutic activities of the compounds. Methods for the production of fusion proteins are known in the art and described, for example, in Ausubel et al (In: Current Protocols in Molecular Biology. Wiley Interscience, ISBN 047 150338, 1987) and Sambrook et al (In: Molecular Cloning: A Laboratory Manual, Cold Spring Harbor Laboratories, New York, Third Edition 2001).

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and/or adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colorings agents. When used in capsule form the capsules may be coated with compounds such as glyceryl monostearate or glyceryl distearate which delay disintegration.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like. The emulsions for oral administration may further comprise one or more emulsifying agents. Suitable emulsifying agents include dispersing agents as exemplified above or natural gums such as guar gum, gum acacia or gum tragacanth.

Timing of Therapies

Those skilled in the art will appreciate that the polyanions may be administered as a single agent or as part of a combination therapy approach to the treatment of sepsis at diagnosis or subsequently thereafter, for example, as follow-up treatment or consolidation therapy as a complement to currently available therapies for sepsis. Patients known to be at high risk of sepsis may also be treated with suitably non-toxic polyanions as part of prophylaxis e.g. together with antibiotics, against development of sepsis.

The invention will now be described in more detail, by way of illustration only, with respect to the following examples. The examples are intended to serve to illustrate this invention and should not be construed as limiting the generality of the disclosure of the description throughout this specification.

EXAMPLES

Example 1

Figure 2A:
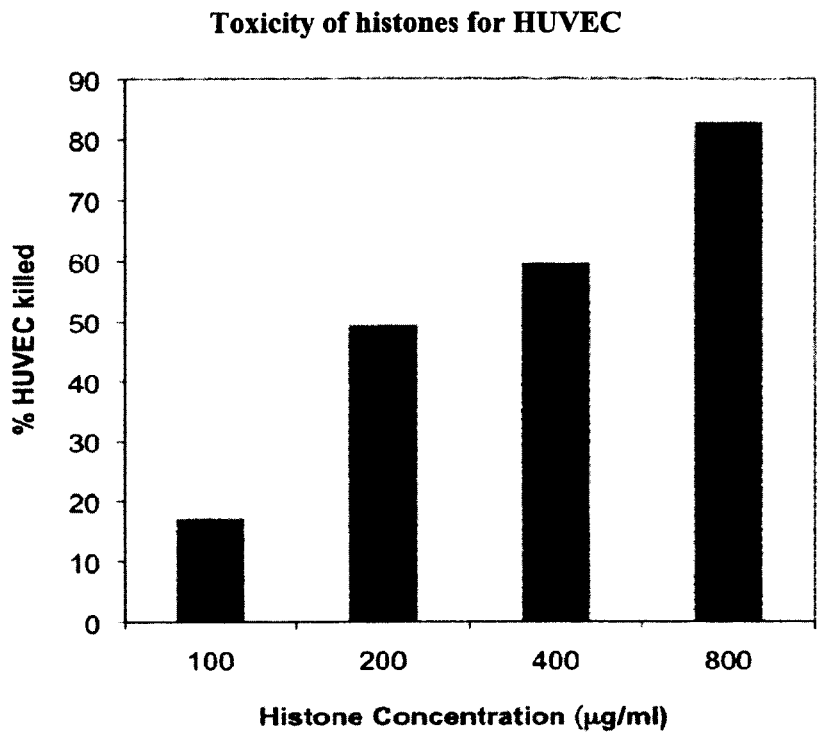
FIG. 2 depicts the ability of different concentrations of calf thymus histones (100-800 μg/ml) to cause the death of (A) HUVEC and (B) human microvascular endothelial cells (HMEC) after 1 hr exposure in vitro.
Figure 2B:
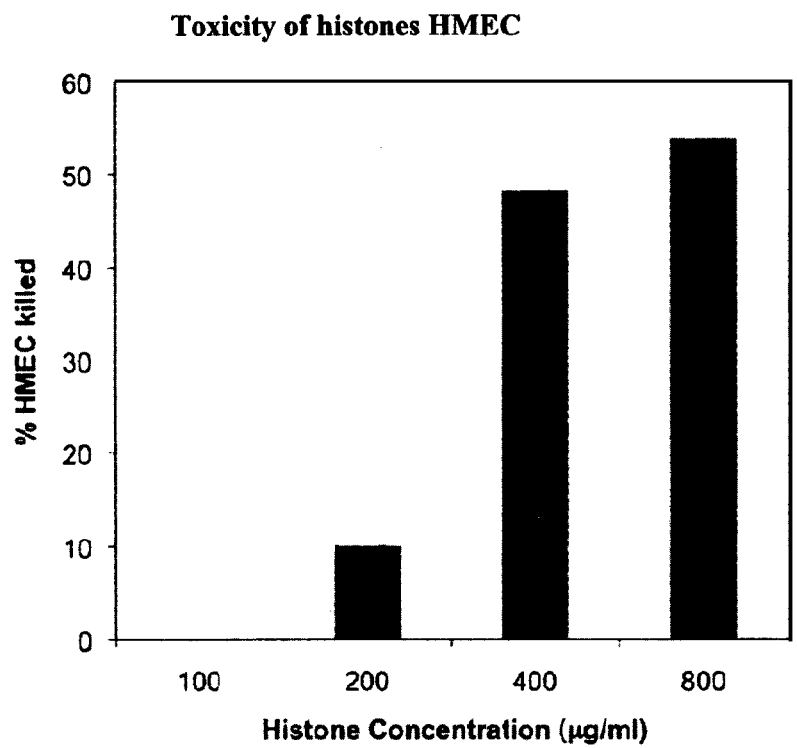

Inhibition by Different Polyanions of the Cytotoxic Action of Histones on Human Endothelial Cells Different concentrations of calf thymus histones were initially assessed for their toxicity for human umbilical vein endothelial cells (HUVEC) and human microvascular endothelial cells (HMEC). Suspensions of HUVEC/HMEC in Medium199/20% fetal calf serum (FCS) were dispensed into each well of a 96 well plate ($1 \times 10^5$ cells/well in 50 µl of medium). Calf thymus histones (50 µl/well in M199/20% FCS) were then added to give a final concentration of 100-800 µg/ml followed by 25 µl/well of Calcein-AM in PBS (final concentration 0.04 µM) and 25 propidium iodide (PI) in PBS (final concentration 2.5 µg/ml). Each 96 well plate was incubated at 37° C. for 60 min in a 5% $CO_2$ incubator, placed on ice and the contents of each well analysed by flow cytometry for viable and dead cells. Viable cells were detected as Calcein-AM-bright and PI-dim and dead cells as Calcein-AM-dim and PI-bright. FIG. 1 depicts a typical viability assay comparing HUVEC cultured alone (9.15% dead, 78.6% viable) with HUVEC cultured for 60 min with 200 µg/ml of calf thymus histones (50.4% dead, 35.6% viable). The toxicity of calf thymus histones for HUVEC and HMEC is shown in detail in FIG. 2, with histone toxicity for HUVEC (FIG. 2A) and HMEC (FIG. 2B) being highly concentration dependent, although HMEC were more resistant to histone toxicity than HUVEC. Thus, at 100 µg/ml histones killed 15-20% of HUVEC but had no effect on HMEC viability, whereas at 800 µg/ml histones killed >85% of HUVEC and ~55% of HMEC (FIG. 1). In subsequent inhibition experiments calf thymus histones were used at 200 µg/ml for HUVEC and 400 µg/ml for HMEC, these concentrations resulting in ~50% killing of both populations of endothelial cells.

Figure 3:
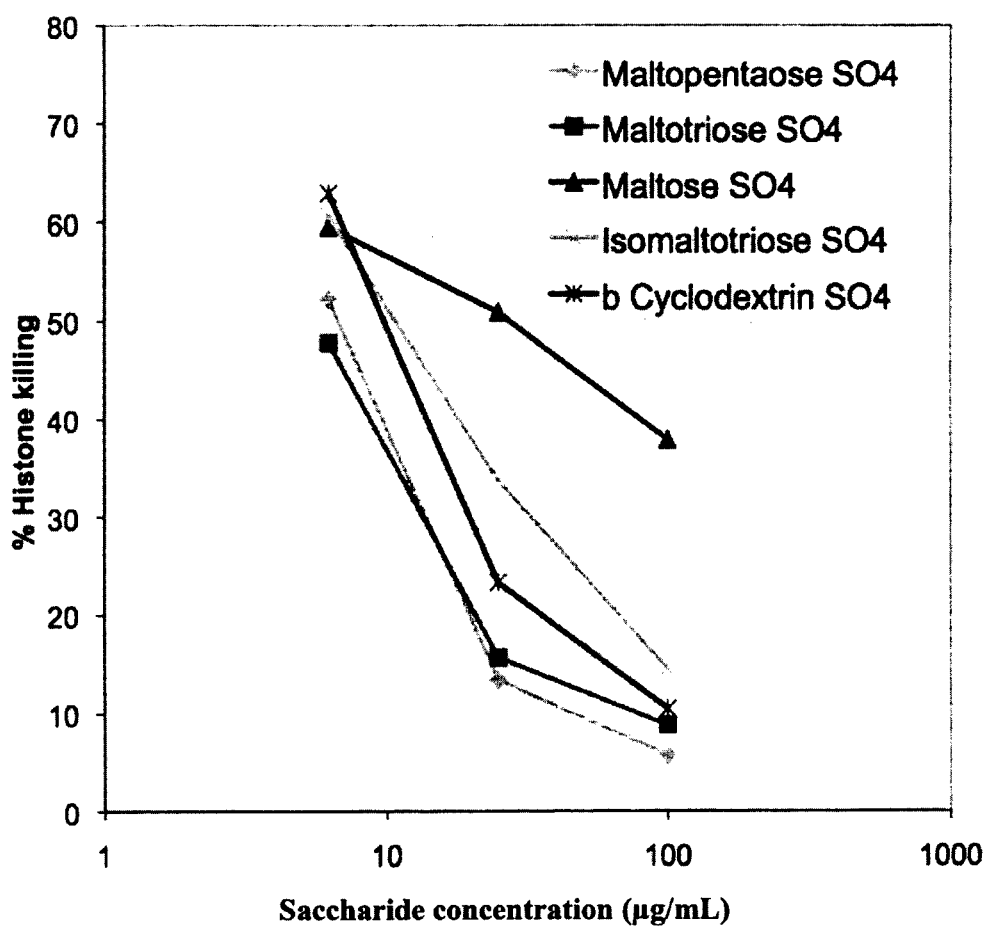
FIG. 3 depicts the ability of different concentrations (6.25-100 μg/ml) of maltose sulfate, maltotriose sulfate, maltopentaose sulfate, isomaltotriose sulfate and β-cyclodextrin sulfate to inhibit the in vitro cytotoxicity of calf thymus histones (200 μg/ml) for HUVEC.
Figure 4:
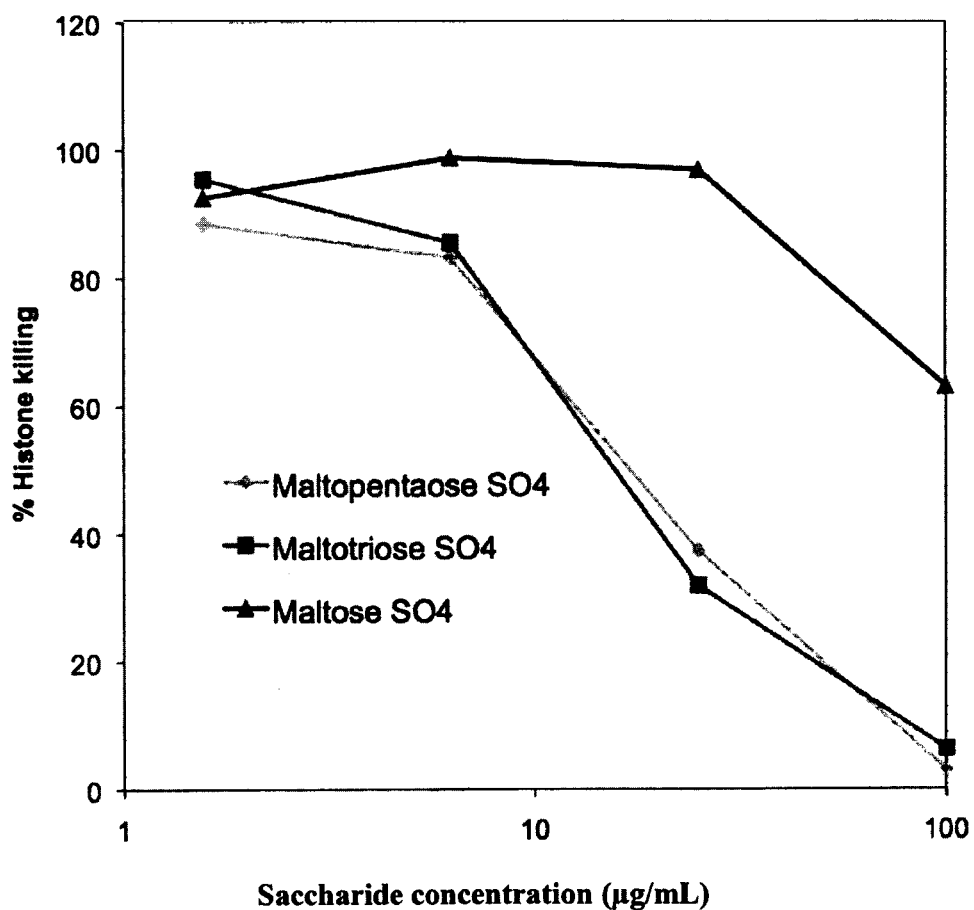
FIG. 4 depicts the ability of a wider concentration range (1.6-100 μg/ml) of maltose sulfate, maltotriose sulfate and maltopentaose sulfate to inhibit the in vitro cytotoxicity of calf thymus histones (200 μg/ml) for HUVEC.

In inhibition experiments the inhibitor (final concentration ranging from 1.6-100 µg/ml) was mixed with calf thymus histones (final concentration 200 or 400 µg/ml) prior to the addition of HUVEC/HMEC, Calcein-AM and PI to each well. It was found that maltotriose sulfate and maltopentaose sulfate were potent inhibitors of histone cytotoxicity for HUVEC, completely inhibiting histone toxicity at 100 µg/ml and still being highly effective at 25 µg/ml (FIGS. 3 and 4). Some of the primary flow cytometry data for maltotriose sulfate is presented in FIG. 5 to further highlight the potent inhibitory activity of this sulfated trisaccharide. In contrast, the disaccharide maltose sulfate was a weak inhibitor of histone cytotoxicity (FIGS. 3 and 4), indicating that with the maltose series of polyanions oligosaccharide chain length plays an important role in inhibitory activity. Isomaltotriose sulfate (α1-6 linked glucose), however, was a less active inhibitor than maltotriose sulfate (α1-4 linked glucose), suggesting that the sugar linkage may also influence inhibitory activity (FIG. 3). However, cyclic β-cyclodextrin sulfate (cyclic α1-4 linked heptaglucose) was almost as active as the linear maltotriose sulfate and maltopentaose sulfate molecules (FIG. 3).

Using HMEC as the endothelial cell target similar inhibitory effects of maltotriose sulfate (FIG. 6) and the other sulfated oligosaccharides (Table 1) on histone toxicity was observed. In fact, a more detailed analysis of the inhibitory activity of a range of polyanions on histone toxicity, using HMEC as the target endothelial cell, is shown in Table 1.

TABLE 1

Ability of different polyanions to inhibit histone killing of HMEC

| Compound | % histone killing ± SEM* |
|---|---|
| Cellobiose SO$_4$ | *6.9 ± 3.3*** |
| Sucrose octasulfate | 43.5 ± 4.0 |
| Maltose SO$_4$ | 77.1 ± 4.7 |
| Maltitol SO$_4$ | *19.6 ± 3.9* |
| Maltotriose SO$_4$ | *17.4 ± 2.8* |
| Isomaltotriose SO$_4$ | 49.5 ± 5.4 |
| Raffinose SO$_4$ | *18.0 ± 3.0* |
| Panose SO$_4$ | *9.3 ± 0.5* |
| Propanyl bis-gluconamide SO$_4$ | 27.8 ± 1.5 |
| Carboxylated β-cyclodextrin | 105.8 ± 19.9 |
| β-cyclodextrin SO$_4$ | *11.7 ± 2.9* |
| Heparin | *2.4 ± 2.1* |
| N-acetylated heparin | 24.8 ± 2.7 |
| Glycol split heparin | *0 ± 1.9* |
| Glycol split N-acetylated heparin | *0 ± 3.1* |
| Enoxaparin | *9.1 ± 5.6* |
| Glycol split Enoxaparin | *0.7 ± 3.3* |
| Glycol split LMWH (3 kDa) | *7.2 ± 1.3* |

*Compounds tested at 50 μg/ml for their ability to inhibit the cytotoxicity of calf thymus histones (400 μg/ml) for HMEC.
**Values in bold and italics represent compounds that inhibited histone toxicity by >80%.
HMEC = human microvascular endothelial cells.
LMWH = low molecular weight heparin.

Different sulfated disaccharides differed in their inhibitory activity, cellobiose sulfate (β1-4 linked glucose) being a potent inhibitor of histone toxicity whereas maltose sulfate (α1-4 linked glucose) and sucrose octasulfate (glucose β1-4 linked fructose) were weaker inhibitors (Table 1). However, the inhibitory activity of maltitol, a 'ring opened form of maltose, was greater than maltose. Sulfated trisaccharides also varied in their inhibitory activity, sulfated maltotriose, raffinose and panose being more active than sulfated isomaltotriose. The analysis also revealed that sulfated linked glucose molecules exhibit some inhibitory activity (e.g., propanyl bis-gluconamide SO$_4$), sulfated β-cyclodextrin is active but carboxylated β-cyclodextrin is not, and heparin, low molecular weight heparin and some chemical variants (e.g., N-deacetylated, glycol split) are active (Table 1).

Figure 7:
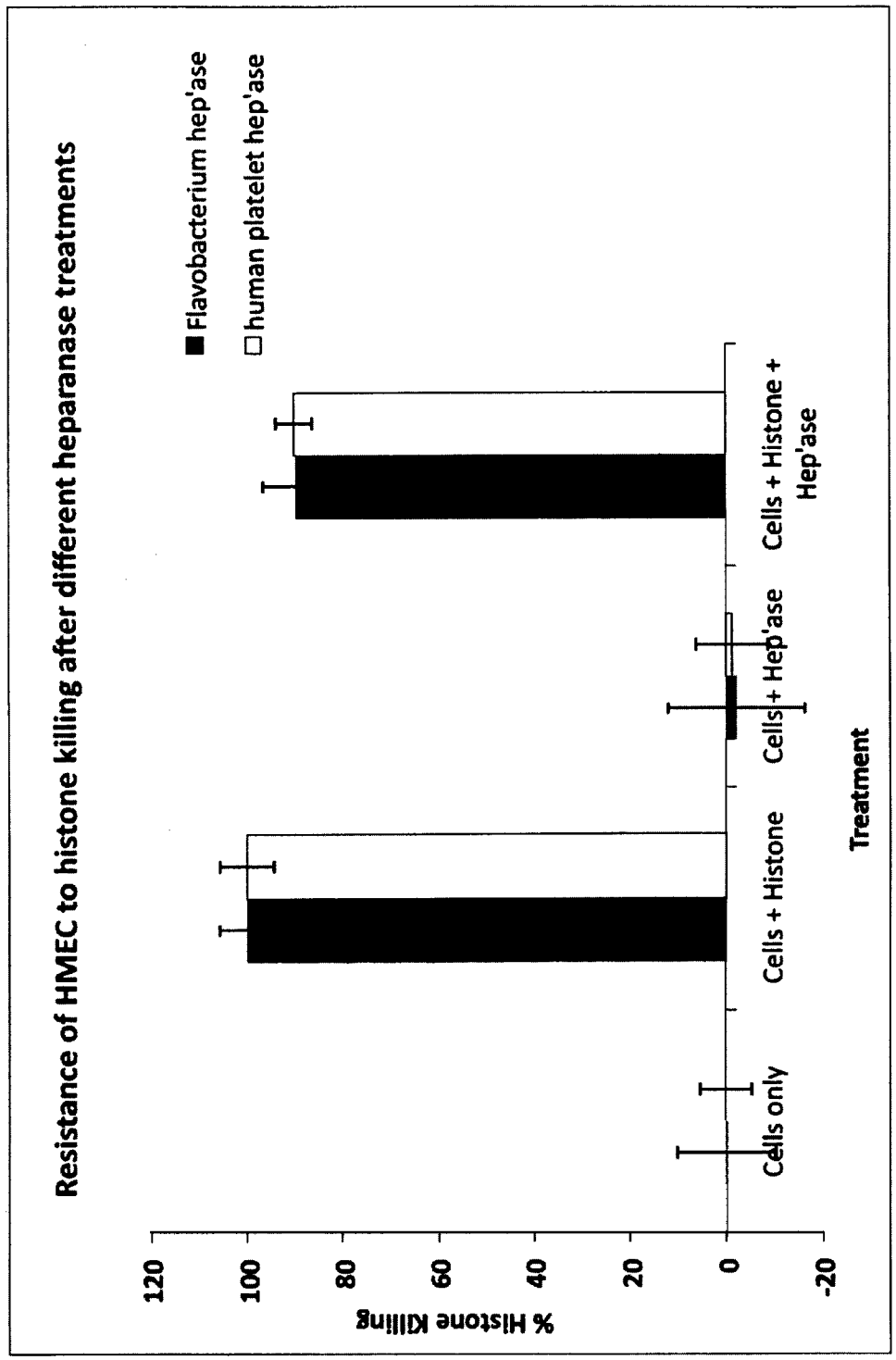
FIG. 7 demonstrates that removal of cell surface heparan sulfate from HMEC with human platelet heparanase or Flavobacterium heparitinase has no effect on the in vitro cytotoxicity of calf thymus histones (400 μg/ml) for HMEC.
Figure 8:
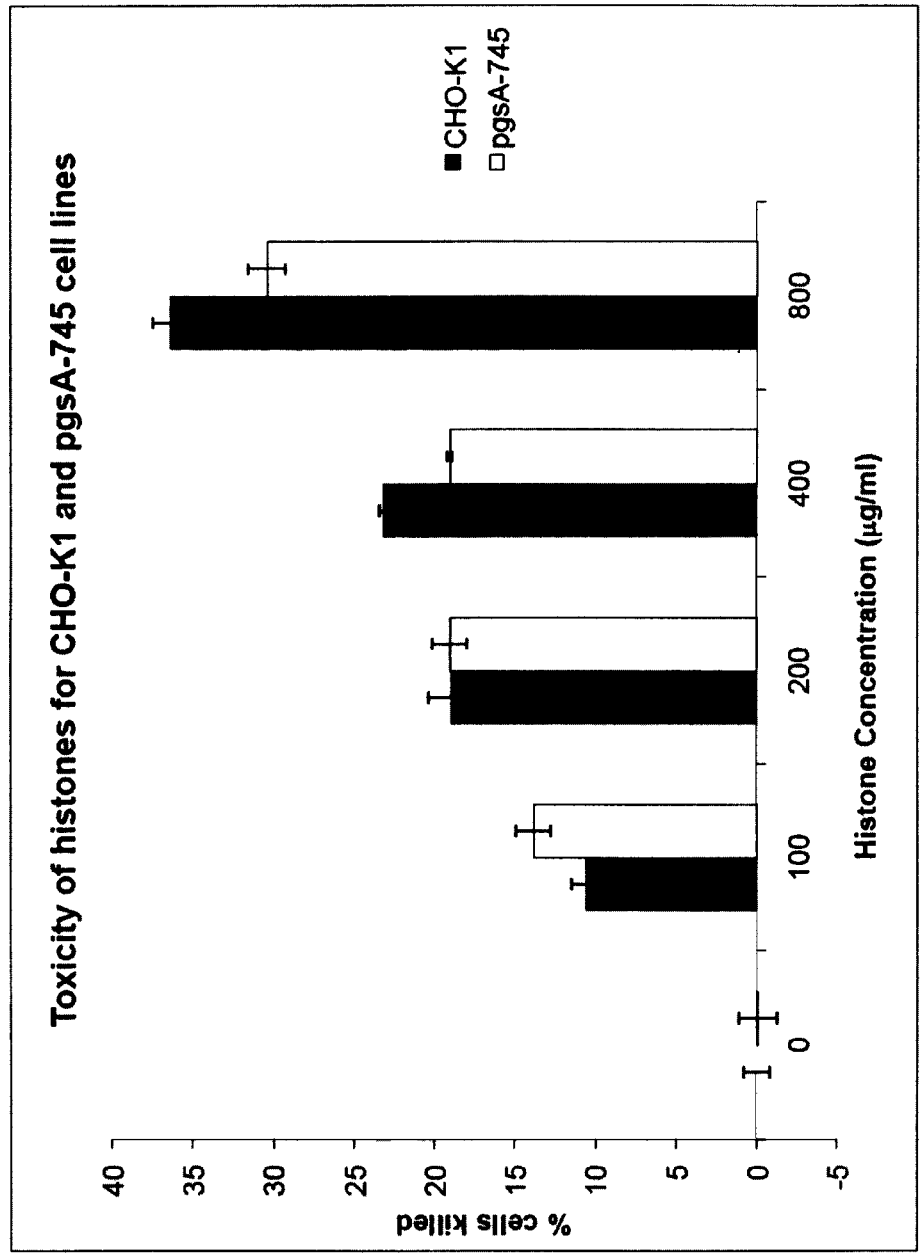
FIG. 8 demonstrates that the wild type CHO-K1 cell line, which expresses cell surface heparan sulfate, and the mutant CHO cell line (pgsA-745) that lacks heparan sulfate, are equally susceptible to the in vitro cytotoxicity of calf thymus histones.

Additional studies revealed that histone cytotoxicity is not dependent on cell surface heparan sulfate. Thus, treatment of HMEC with human platelet heparanase (4 μg/ml, 37° C., 1 hr) or heparitinase I, II and III from *Flavobacterium heparinum* (0.25 units/ml, is 37° C., 1 hr), enzymatic procedures that remove cell surface heparan sulfate, had no effect on the susceptibility of HMEC to histone cytotoxicity (FIG. 7). Similarly, comparison of wild type chinese hamster ovary (CHO-K1) cells and a heparan sulfate deficient variant of this cell line (pgsA-745), revealed that both cell lines are equally susceptible to histone cytotoxicity (FIG. 8).

Example 2

Intravenously Injected Histones Accumulate in the Lungs of Rabbits

Figure 9A:
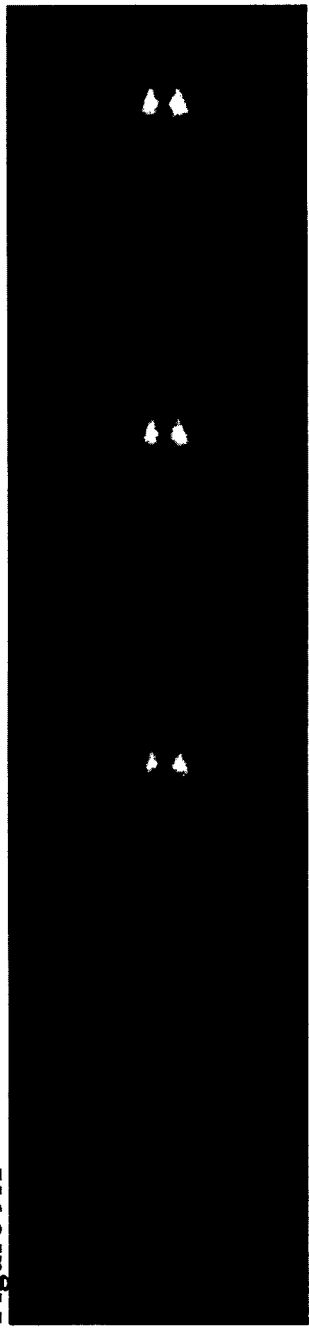
FIG. 9A is a series of 30 second acquisitions from gamma scintigraphy, commencing from the beginning of the injection of histones labelled with Tc99m-nanoparticles into the ear vein of an anaesthetised rabbit.
Figure 9B:
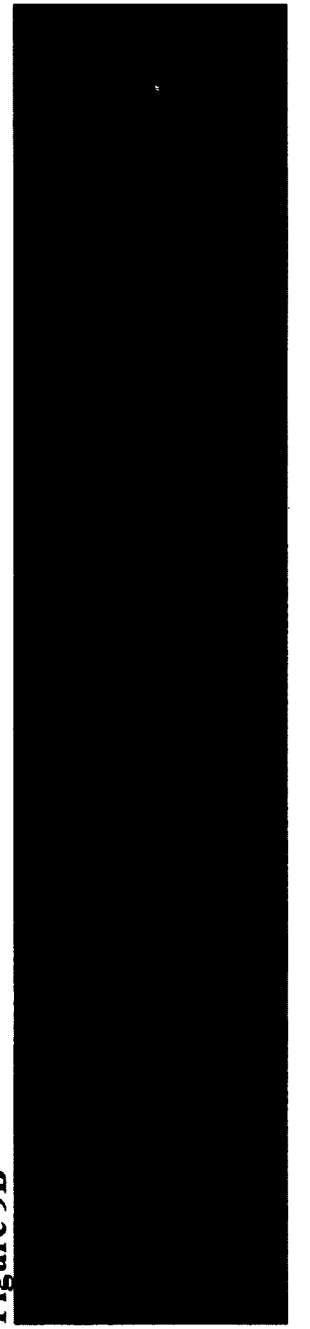
FIG. 9B is a series of 30 second acquisitions from gamma scintigraphy, commencing from the beginning of the injection of Tc99m-nanoparticles into the ear vein of an anaesthetised rabbit.

Calf thymus histones were radiolabelled by adsorption onto the surface of Tc99m-nanoparticles. An aqueous colloidal suspension (3 mL) of Tc99m-nanoparticles (approx 50 μg; 4 mCi) were treated with histones (10 μg/mL) for 1 hour at room temperature. The radiolabelled histones were injected into an ear vein of an anaesthetised rabbit placed under a gamma camera, and dynamic images were obtained as a series of 30 second acquisitions, commencing from the beginning of the injection. The images in FIG. 9A show rapid and selective accumulation of histones in the lung, consistent with lung localisation of histone-induced tissue damage. Radiolabelled nanoparticles without histones bound localised in the liver, spleen and bone marrow (see FIG. 9B), as expected for rapid clearance of circulating foreign particles by the reticuloendothelial system.

Example 3

Competitive Inhibition of Histone Accumulation in Lung

Figure 10A:
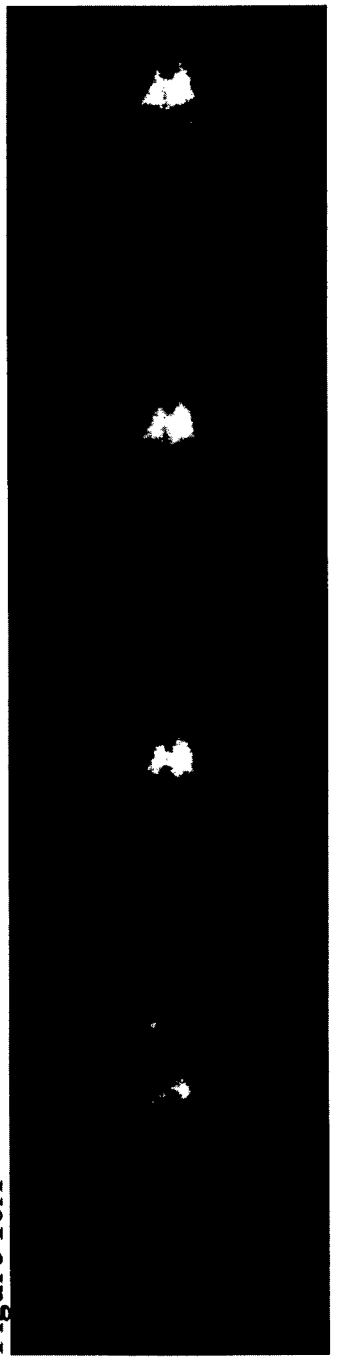
FIG. 10A is a series of 30 second acquisitions from gamma scintigraphy, commencing from the beginning of the injection of histones labelled with Tc99m-nanoparticles into the ear vein of an anaesthetised rabbit.
Figure 10B:
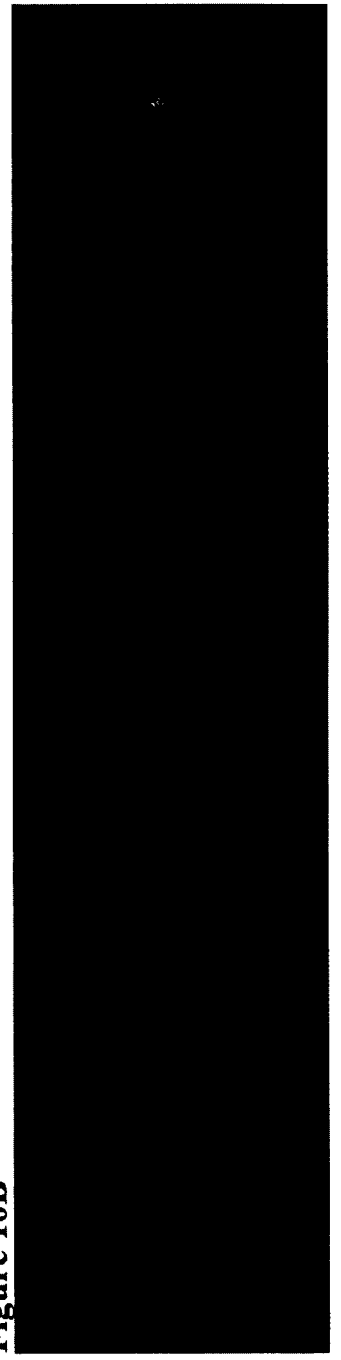
FIG. 10B is a series of 30 second acquisitions from gamma scintigraphy, commencing from the beginning of the injection of histones labelled with Tc99m-nanoparticles into the ear vein of an anaesthetised rabbit pretreated with 15 mg/kg of sodium maltohexaose sulfate.

Calf thymus histones were radiolabelled by adsorption onto the surface of Tc99m-nanoparticles. This radiolabelled preparation was then divided in half. The first half was injected into an ear vein of an anaesthetised control rabbit placed under a gamma camera, and dynamic images were obtained as a series of 30 second acquisitions, commencing from the beginning of the injection. As in Example 2 above, the images in FIG. 10A show rapid and selective accumulation of radiolabelled histones in the lung of the control rabbit. The second half of the radiolabelled histone preparation was injected into an ear vein of an anaesthetised rabbit that had been injected intravenously 15 minutes earlier with 15 mg/kg of sodium maltohexaose sulfate. Gamma imaging of this pretreated rabbit from the beginning of the injection of radiolabel showed that accumulation of radiolabelled histones in the lung was blocked (FIG. 10B). The radiolabelled histone passed through the lungs and localised in the liver and spleen.

Example 4

Blockade of Histone Accumulation in Rabbit Lungs by Maltotetraose Sulfate

Figure 11:
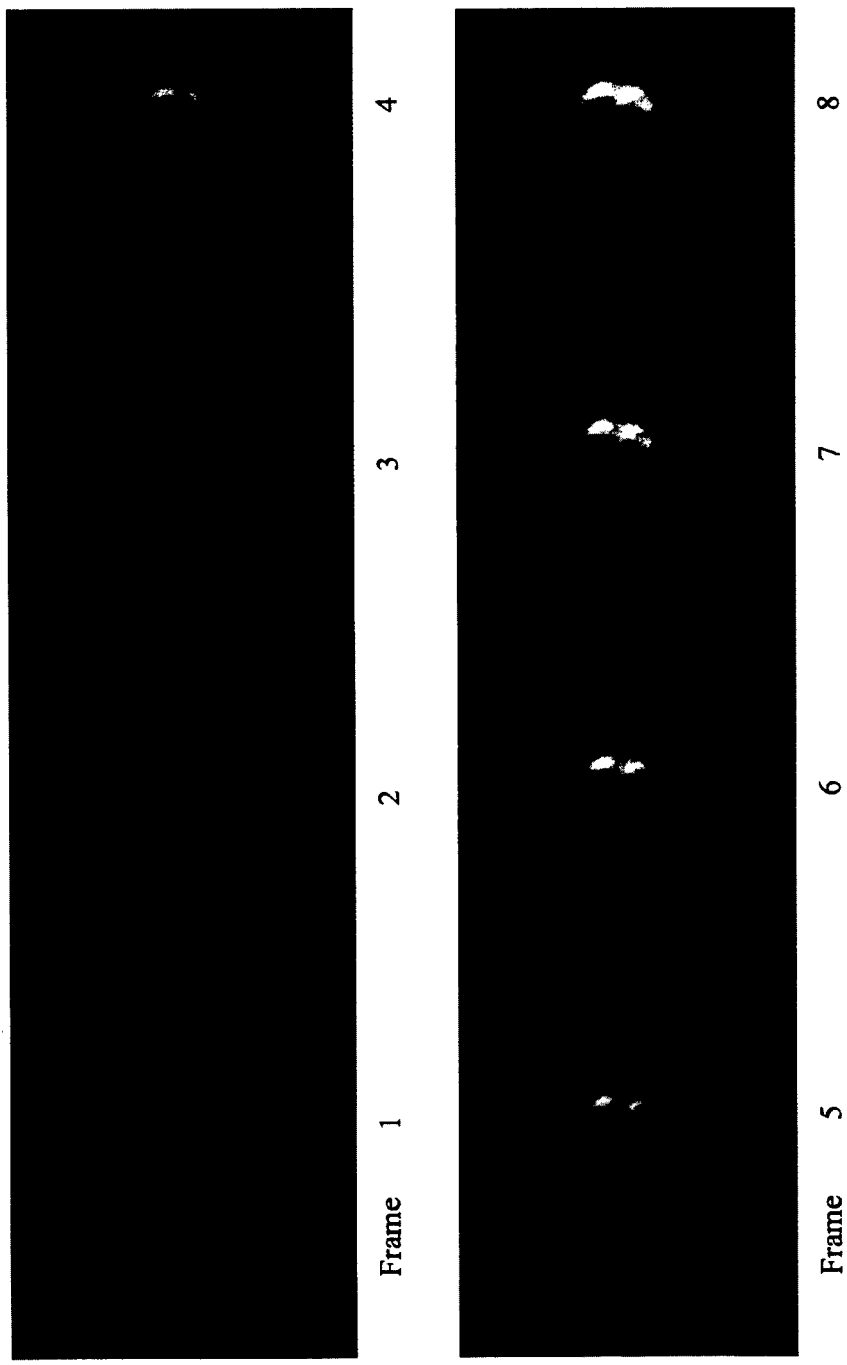
FIG. 11 is a series of 30 second acquisitions (frames 1-4) and 60 second acquisitions (frames 5-8) from gamma scintigraphy commencing from the beginning of the injection of histones labelled with Tc99m-nanoparticles into the ear vein of an anaesthetised rabbit pretreated with 15 mg/kg of sodium maltotetraose sulfate.

A radiolabelled histone preparation was injected into an ear vein of an anaesthetised rabbit that had been injected intravenously 15 minutes earlier with 15 mg/kg of sodium maltotetraose sulfate. Gamma imaging of this pretreated rabbit (FIG. 11) from the beginning of the injection of radiolabel showed that accumulation of radiolabelled histones in the lungs was blocked; the radiolabelled histone passed through the lungs without binding and localised in the liver and spleen. Frames 1-4 of FIG. 11 are 30 second acquisitions, while frames 5-8 are 60 second acquisitions.

Example 5

Blockade of Histone Accumulation in Rabbit Lungs by Cellobiose Sulfate

Figure 12:
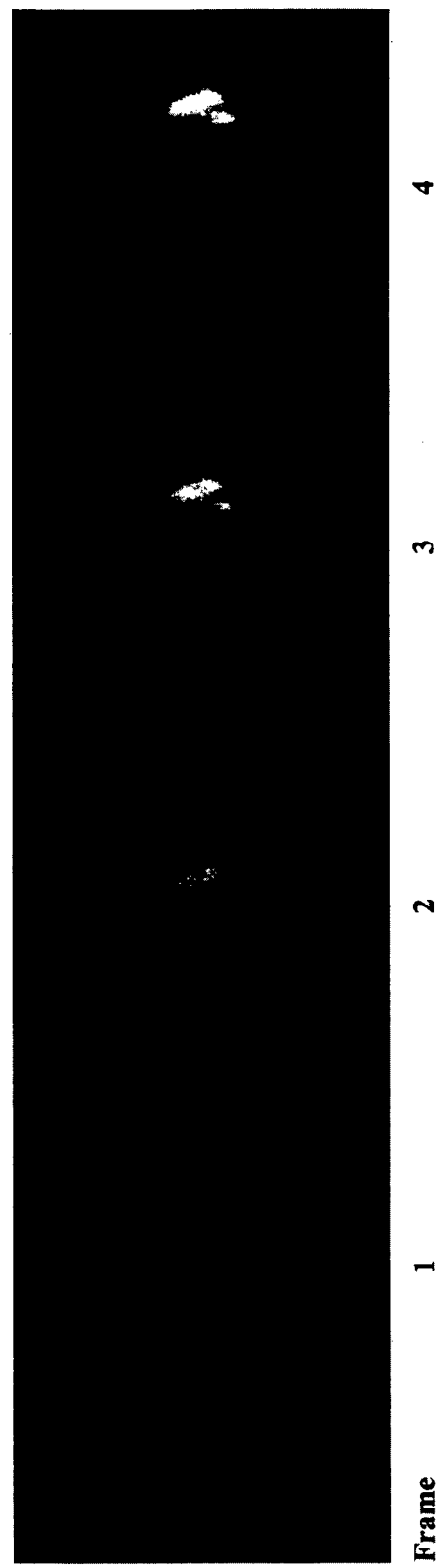
FIG. 12 is a series of 30 second acquisitions from gamma scintigraphy commencing from the beginning of the injection of histones labelled with Tc99m-nanoparticles into the ear vein of an anaesthetised rabbit pretreated with 15 mg/kg of sodium cellobiose sulfate.

A radiolabelled histone preparation was injected into an ear vein of an anaesthetised rabbit that had been injected intravenously 15 minutes earlier with 15 mg/kg of sodium cellobiose sulfate. Gamma imaging of this pretreated rabbit (FIG. 12) from the beginning of the injection of radiolabel showed that accumulation of radiolabelled histones in the lungs was blocked; the radiolabelled histone passed through the lungs without binding and localised in the liver and spleen. Frames 1-4 of FIG. 12 are 30 second gamma camera acquisitions.

Example 6

LPS-Induced Sepsis Study in Mice

A study was conducted to assess in vivo efficacy of test articles 1 (maltotriose sulfate; TA1), 2 (cellobiose sulfate; TA2), and 3 (heparin; TA3) in a lipopolysaccharide (LPS)-induced mouse model of sepsis. Endotoxemia was induced by intraperitoneal (i.p.) injection with LPS on day 1. Test articles were co-administered i.p. on day 1, and then dosed daily i.p. for an additional 2 days. Test articles 1 and 2 were evaluated at 2 dose concentrations, and test article 3 at one concentration as shown in Table 2 below.

TABLE 2

| Group | Treatment | Dose Level (mass/injection) | Dose Route | No. Animals |
|---|---|---|---|---|
| 1 | vehicle control (PBS) | — | i.p. | 8 Females |
| 2 | test article 1 | high dose 100 mg/kg (initial + 24 hr from previous dose on d2 and d3) | i.p. | 8 Females |
| 3 | test article 1 | low dose 15 mg/kg (initial + 24 hr from previous dose on d2 and d3) | i.p. | 8 Females |
| 4 | test article 2 | high dose 100 mg/kg (initial + 24 hr from previous dose on d2 and d3) | i.p. | 8 Females |
| 5 | test article 2 | low dose 15 mg/kg (initial + 24 hr from previous dose on d2 and d3) | i.p. | 8 Females |
| 6 | test article 3 | low dose 1.1 mg/kg (initial + 24 hr from previous dose on d2 and d3) | i.p. | 8 Females |

RESULTS

Figure 13:
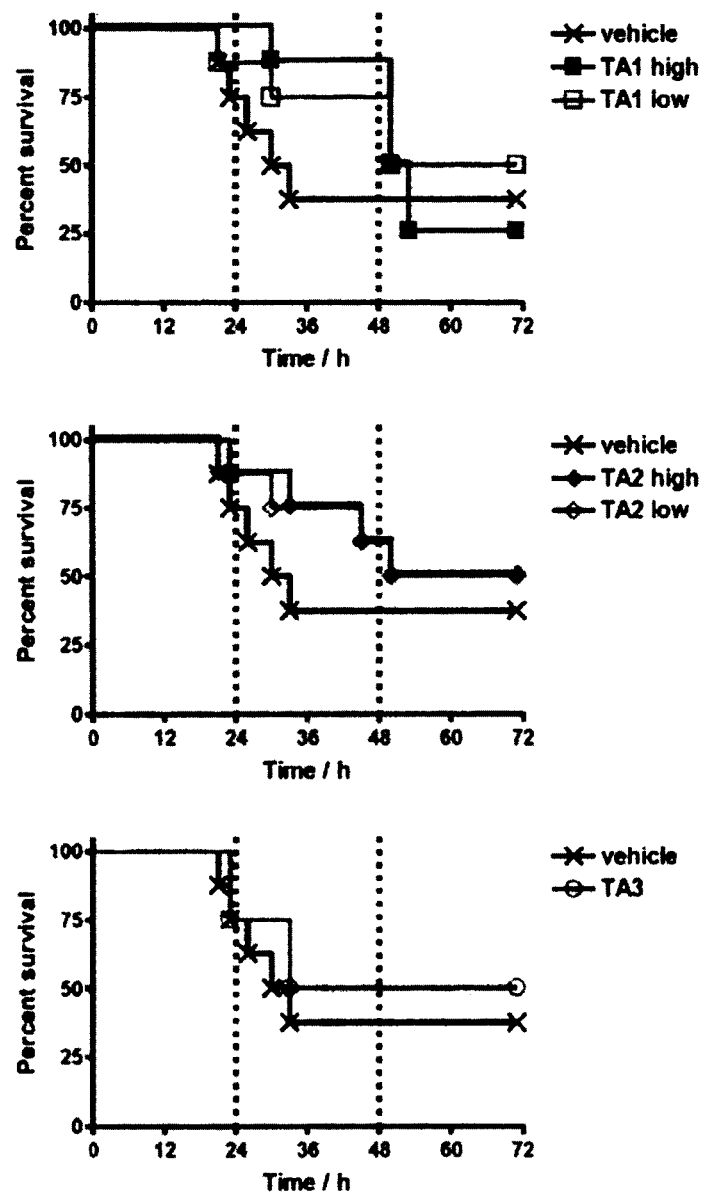
FIG. 13 is a Kaplan-Meier survival plot for a lipopolysaccharide (LPS)-induced mouse model of sepsis and assessment of in vivo efficacy of test articles 1 (maltotriose sulfate; TA1), 2 (cellobiose sulfate; TA2), and 3 (heparin; TA3. Test articles were co-administered i.p. on day 1 with LPS (50 mg/kg), and then dosed daily i.p. for an additional 2 days. Test articles 1 and 2 were evaluated at 2 dose concentrations (high dose, 100 mg/kg and low dose, 15 mg/kg), and test article 3 at one dose (1.1 mg/kg). Events marked on the plot record the times until mice were found dead or had to be euthanized.

The times until animals were either found dead, or had to be euthanized, are shown in the Kaplan-Meier plot in FIG. 13. The high dose (100 mg/kg) of maltotriose sulfate (TA1) used in this study appeared to produce some toxicity (cluster of deaths) after the third dose, but the low dose (15 mg/kg) was better tolerated. Cellobiose sulfate (TA2) at both doses was well tolerated, as was the low dose chosen for heparin (TA3; 1.1 mg/kg). The Kaplan-Meier plots in FIG. 13 indicated that extended survival was obtained for the low dose of maltotriose sulfate (TA1) and both doses of cellobiose sulfate (TA2). In the case of heparin (TA3), there was no apparent change in the survival plot compared to the control (see FIG. 13).

The invention claimed is:

1. A method of treating sepsis by inhibiting the cytotoxic activity of extracellular histones in a subject having sepsis, said method comprising administering an effective amount of a polyanion to said subject, wherein the polyanion does not have substantial anticoagulant activity; and
wherein the polyanion is a polyanionic oligosaccharide having the general structure (I):

wherein A and B are each independently a cyclic monosaccharide or a cyclic deoxy monosaccharide;
D is a cyclic monosaccharide, a cyclic deoxy monosaccharide, a ring-opened monosaccharide, or a sugar alcohol;
n is an integer selected from 0, 1, and 2; and
wherein each of the cyclic monosaccharide, the cyclic deoxy monosaccharide, the ring-opened monosaccharide, or the sugar alcohol is independently optionally substituted with $OSO_3^-$, $COO^-$, $OPO_3^-$, an optionally substituted alkyl, an optionally substituted alkenyl, an optionally substituted alkynyl, an optionally substituted aryl, or an optionally substituted aralkyl; and
wherein the polyanionic oligosaccharide includes at least two anionic substituents selected from the group consisting of $OSO_3^-$, $COO^-$ and $OPO_3^-$; and
wherein the polyanion does not have substantial anticoagulant activity if the polyanion increases prothrombin time (PT), partial thromboplastin time (PTT), activated partial thromboplastin time (APTT), thrombin clotting time (TCT), or activated clotting time (ACT) by 0 to 10% of the normal range.

2. The method of claim 1 wherein the polyanion is substantially non-immunogenic.

3. The method of claim 1 wherein the cyclic monosaccharide is selected from the group consisting of glucose, galactose, fructose, ribose, arabinose, xylose, lyxose, allose, altrose, mannose, gulose, idose, talose, ribulose, xylulose, psicose, sorbose, tagatose and sedoheptulose.

4. The method of claim 3 wherein the cyclic monosaccharide is selected from the group consisting of glucose, galactose and fructose.

5. The method of claim 1 wherein the cyclic deoxy monosaccharide is selected from the group consisting of fucose, deoxyribose and rhamnose.

6. The method of claim 1 wherein the sugar alcohol is selected from the group consisting of glycol, glycerol, erythritol, threitol, ribitol, arabitol, xylitol, sorbitol (glucitol), mannitol, dulcitol (galactitol), iditol and fucitol.

7. The method of claim 1 wherein the ring-opened monosaccharide is selected from the group consisting of glucose, galactose, fructose, erythrose, threose, erythrulose, ribose, arabinose, xylose, lyxose, allose, altrose, mannose, gulose, idose, talose, ribulose, xylulose, psicose, sorbose, tagatose and sedoheptulose.

8. The method of claim 1 wherein the polyanionic oligosaccharide has the general structure (I-a):

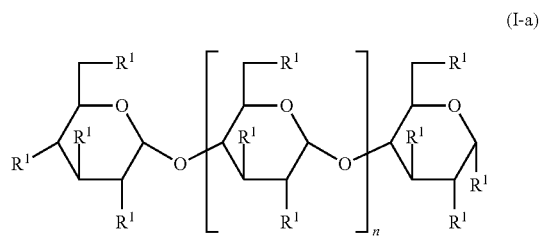

wherein each $R^1$ is independently selected from $OSO_3^-$, $COO^-$, $OPO_3^-$, OH or H; and n is an integer between 0, 1, and 2; and wherein at least two of $R^1$ are selected from the group consisting of $OSO_3^-$, $COO^-$, and $OPO_3^-$.

9. The method of claim 1 wherein the polyanionic oligosaccharide has the general structure (I-b):

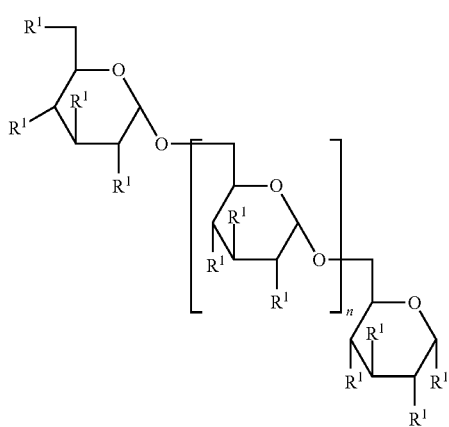

(I-b)

where each $R^1$ is independently selected from $OSO_3^-$, $COO^-$, $OPO_3^-$, OH or H; and n is an integer between 0, 1, and 2; and wherein at least two of $R^1$ are selected from the group consisting of $OSO_3^-$, $COO^-$, and $OPO_3^-$.

10. The method of claim 1 wherein the polyanionic oligosaccharide is selected from the group consisting of:

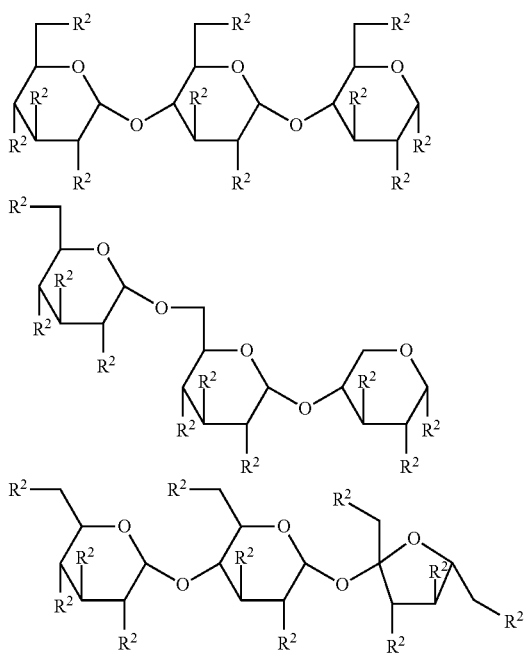

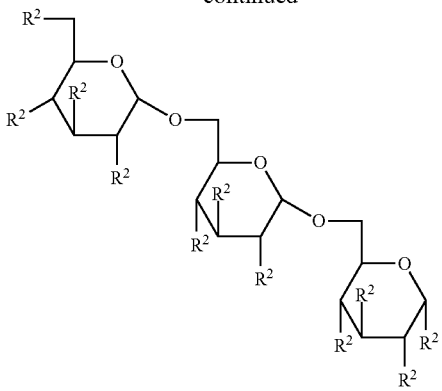

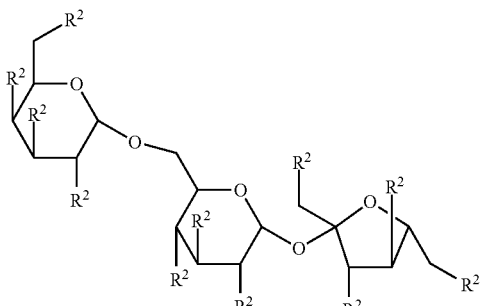

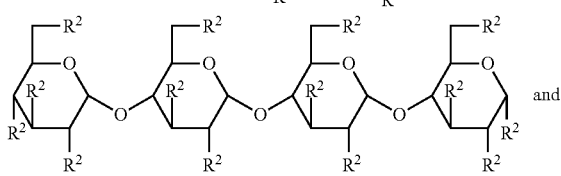 and

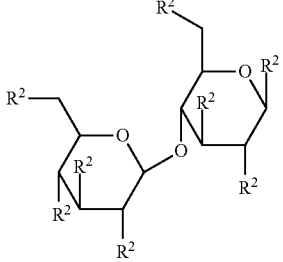

wherein each $R^2$ is independently selected from $OSO_3^-$, $COO^-$, $OPO_3^-$, OH or H; and wherein at least two of $R^2$ are selected from the group consisting of $OSO_3^-$, $COO^-$, and $OPO_3^-$.

11. The method of claim 1 wherein the polyanionic oligosaccharide is selected from the group consisting of maltose sulfate, maltotriose sulfate, maltotetraose sulfate, panose sulfate, isomaltotriose sulfate, erlose sulfate, cellobiose sulfate and raffinose sulfate.

12. The method of claim 1 wherein the polyanionic oligosaccharide is cellobiose sulfate.

\* \* \* \* \*